US011673966B2

(12) United States Patent
Zhou et al.

(10) Patent No.: US 11,673,966 B2
(45) Date of Patent: Jun. 13, 2023

(54) MONOCLONAL AND HUMANIZED ANTIBODIES TO A CANCER GLYCOPEPTIDE

(71) Applicants: NanoCruise Pharmaceutical Ltd., Jiangsu (CN); Board of Regents of The University of Texas System, Austin, TX (US)

(72) Inventors: Dapeng Zhou, Jiangsu (CN); Patrick Hwu, Houston, TX (US)

(73) Assignees: NanoCruise Pharmaceutical Ltd., Jiangsu (CN); Board of Regents of The University of Texas System, Austin, TX (US)

(*) Notice: Subject to any disclaimer, the term of this patent is extended or adjusted under 35 U.S.C. 154(b) by 253 days.

(21) Appl. No.: 16/478,833

(22) PCT Filed: Jan. 18, 2017

(86) PCT No.: PCT/CN2017/071546
§ 371 (c)(1),
(2) Date: Jul. 17, 2019

(87) PCT Pub. No.: WO2018/132976
PCT Pub. Date: Jul. 26, 2018

(65) Prior Publication Data
US 2020/0115466 A1    Apr. 16, 2020

(51) Int. Cl.
*C07K 16/30* (2006.01)
*A61P 35/00* (2006.01)
*C07K 16/46* (2006.01)
*A61K 39/00* (2006.01)

(52) U.S. Cl.
CPC .......... *C07K 16/3092* (2013.01); *A61P 35/00* (2018.01); *C07K 16/464* (2013.01); *A61K 2039/505* (2013.01); *C07K 2317/24* (2013.01); *C07K 2317/565* (2013.01)

(58) Field of Classification Search
CPC ............ C07K 16/3092; C07K 2317/24; C07K 2317/565; A61K 2039/505
USPC ..................................... 424/133.1
See application file for complete search history.

(56) References Cited

U.S. PATENT DOCUMENTS

| 9,469,876 | B2* | 10/2016 | Kuslich | ............ | G01N 33/57419 |
| 2012/0128676 | A1 | 5/2012 | Goletz et al. | | |
| 2014/0141986 | A1* | 5/2014 | Spetzler | ................. | G01N 33/50 |
| | | | | | 506/9 |
| 2014/0148350 | A1* | 5/2014 | Spetzler | ............... | G01N 33/574 |
| | | | | | 506/9 |
| 2014/0162888 | A1* | 6/2014 | Kuslich | ............ | G01N 33/57419 |
| | | | | | 506/9 |
| 2015/0301055 | A1* | 10/2015 | Spetzler | ........... | G01N 33/57484 |
| | | | | | 506/9 |
| 2020/0010795 | A1* | 1/2020 | Wu | ..................... | C07K 16/2803 |

FOREIGN PATENT DOCUMENTS

| CN | 103880956 A | 6/2014 |
| JP | 2013500703 A | 1/2013 |
| JP | 2016525560 A | 8/2016 |
| WO | 2011012309 A1 | 2/2011 |
| WO | 2015014879 A1 | 2/2015 |

OTHER PUBLICATIONS

Heublein et al. (Journal of Cancer Research and Clinical Oncology (2018) 144:1899-1907).*
Chopra (Molecular Imaging and Contrast Agent Database (MICAD) [Internet], Bethesda (MD): National Center for Biotechnology Information (US); 2004-2013 (Jun. 16, 2011 [updated Jul. 26, 2011])).*
Gong et al (Cancers 13: 2579-2598 (May 21, 2021)).*
Kunin et al. (American University Law Review 51(4): 609-638 (Apr. 2002)).*
Qu et al. (International Journal of Oncology 48: 587-594, 2016).*
Pan et al (Cancer Med. 2020;9: 9529-9540).*
Fternational Search Report corresponding to International application No. PCT/CN2017/071546, dated Oct. 24, 2017, 5 pages.
Written Opinion corresponding to International application No. PCT/CN2017/071546, dated Oct. 24, 2017, 4 pages.
E. Pichinuk et al., "Antibody Targeting of Cell-Bound MUC1 SEA Domain Kills Tumor Cells", Cancer Research, vol. 72, No. 13, dated Jul. 1, 2012, pp. 3324-3336.
W. Song et al. "MUC1 Glycopeptide Epitopes Predicted by Computational Glycomics", International Journal of Oncology (2012), vol. 41, No. 6, Sep. 27, 2012, pp. 1977-1984.
X. Fan et al. "Reactivity of a Humanized Antibody (hPankoMab) Towards a Tumor-Related MUC1 Epitope (TA-MUC1) with Various Human Carcinomas", Pathology—Research and Practice, vol. 206, No. 8, Aug. 15, 2010, pp. 585-589.

(Continued)

*Primary Examiner* — Lynn A Bristol
(74) *Attorney, Agent, or Firm* — Reising Ethington P.C.

(57) ABSTRACT

The present invention discloses a mouse-human chimeric antibody preferably recognizes the MUC1 glycopeptide epitope RPAPGS(GalNAc)TAPPAHG (SEQ ID NO.: 34) on the surface of cancer cells, and the encoding sequences, wherein the monoclonal antibody having a light chain and a heavy chain. Moreover, the present invention provides humanized light and heavy chains, and the encoding sequences. The results of paired expression show that humanized antibodies also recognize the MUC1 glycopeptide epitope RPAPGS(GalNAc)TAPPAHG (SEQ ID NO.: 34) on the surface of cancer cells, and show the same specificity as the parental antibody.

13 Claims, 15 Drawing Sheets
Specification includes a Sequence Listing.

(56) References Cited

OTHER PUBLICATIONS

W. Fiedler et al. "A Phase I Study of PankoMab-GEX, A Humanised Glyco-Optimised Monoclonal Antibody to a Novel Tumour-Specific MUC1 Glycopeptide Epitope in Patients with Advanced Carcinomas", European Journal of Cancer, vol. 63, Jun. 7, 2016, pp. 55-63.

European Search Report corresponding to European Application No. EP 17 89 2372, dated Jul. 21, 2020, 12 pages.

English translation of an Office Action in counterpart Japanese Patent Application No. 2019-559134, dated Aug. 31, 2021, 6 pages.

English translation of an Office Action in counterpart Japanese Patent Application No. 2019-559134, dated 5 Apr. 5, 6 pages.

\* cited by examiner

The amino acid sequence of heavy chain of chimeric 16A

SEQ ID NO.:1, 159-16A-1-hIgG1 HC [H2267]:
MDPKGSLSWRILLFLSLAFELSYGEVKLHQSGGGLVQPGGFLKISCVVSGIDFSRYWMSWVRRAPGKGLEWIGEI
TPDSNTINYVPSLKDNFGISRDNAKNTLFLQMTKVRSEDTALYFCASYYEGFAYWGQGTLVTVSAASTKGPSVFP
LAPSSKSTSGGTAALGCLVKDYFPEPVTVSWNSGALTSGVHTFPAVLQSSGLYSLSSVVTVPSSSLGTQTYICNV
NHKPSNTKVDKKVEPKSCDKTHTCPPCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKALPAPIEKTISKAKGQPREPQVYTLP
PSRDELTKNQVSLTCLVKGFYPSDIAVEWESNGQPENNYKTTPPVLDSDGSFFLYSKLTVDKSRWQQGNVFSCSV
MHEALHNHYTQKSLSLSPG*

The amino acid sequence of light chain of chimeric 16A

SEQ ID NO.:2, 159-16A-1-hLambda 2 LC [L2267]:
MSVPTQVLGLLLLWLTDARCQAVVTQESALTTSPGETVTLTCRSSTGAVITSNYANWVQEKPDHLFTGLIGRTYN
RVPGVPARFSGSLIGDKAALTITGAQTEDEAIYFCALWYSNHFVFGGGTKLTVLGQPKAAPSVTLFPPSSEELQA
NKATLVCLISDFYPGAVTVAWKADSSPVKAGVETTTPSKQSNNKYAASSYLSLTPEQWKSHRSYSCQVTHEGSTV
EKTVAPTECS*

Variable region

The amino acid sequence of variable region of heavy chain of chimeric 16A

SEQ ID NO.:19, 159-16A-1-hIgG1 HC [VH2267]:
EVKLHQSGGGLVQPGGFLKISCVVSGIDFSRYWMSWVRRAPGKGLEWIGEITPDSNTINYVPSLKDNFGISRDNA
KNTLFLQMTKVRSEDTALYFCASYYEGFAYWGQGTLVTVSA

The amino acid sequence of variable region of light chain of chimeric 16A

SEQ ID NO.:20, 159-16A-1-hLambda 2 LC [VL2267]:
QAVVTQESALTTSPGETVTLTCRSSTGAVITSNYANWVQEKPDHLFTGLIGRTYNRVPGVPARFSGSLIGDKAAL
TITGAQTEDEAIYFCALWYSNHFVFGGGTKLTVL

Fig. 3

The DNA sequence of heavy chain of chimeric 16A

SEQ ID NO.:3, 159-16A-1-hIgG1 HC [H2267]:
ATGGACCCCAAGGGCAGCCTGAGCTGGAGAATCCTGCTGTTCCTGAGCCTGGCCTTCGAGCTGAGCTACGGCGAG
GTGAAGCTTCACCAGTCTGGAGGTGGCCTGGTGCAGCCTGGAGGATTCCTGAAAATCTCCTGTGTAGTCTCAGGA
ATCGATTTTAGTAGATACTGGATGAGTTGGGTTCGGCGGGCTCCAGGGAAAGGACTAGAATGGATTGGAGAAATT
ACTCCAGATAGCAATACAATAAACTATGTACCATCTCTAAAGGATAATTTCGGCATCTCCAGAGACAACGCCAAA
AATACGCTGTTCCTGCAAATGACCAAAGTGAGATCTGAGGACACAGCCCTTTATTTCTGTGCATCCTACTACGAG
GGATTTGCTTACTGGGGCCAAGGGACTCTGGTCACTGTCTCTGCAGCTAGCACCAAGGGCCCCAGCGTGTTCCCT
CTGGCCCCCAGCAGCAAGAGCACCAGCGGCGGAACCGCCGCCCTGGGCTGCCTGGTGAAGGACTACTTCCCCGAG
CCCGTGACCGTGTCCTGGAACAGCGGCGCTCTGACCAGCGGAGTGCACACCTTCCCTGCCGTGCTGCAGAGCAGC
GGCCTGTACTCCCTGAGCAGCGTGGTGACCGTGCCCAGCAGCAGCCTGGGCACCCAGACCTACATCTGCAACGTG
AACCACAAGCCCTCCAACACCAAGGTGGACAAGAAGGTGGAGCCTAAGAGCTGCGACAAGACCCACACCTGCCCT
CCCTGCCCCGCCCCCGAGCTGCTGGGCGGACCCAGCGTGTTCCTGTTCCCTCCCAAGCCCAAGGACACCCTGATG
ATCAGCCGCACCCCCGAGGTGACCTGCGTGGTGGTGGACGTGAGCCACGAGGACCCCGAGGTGAAGTTCAACTGG
TACGTGGACGGCGTGGAGGTGCACAACGCCAAGACCAAGCCTCGGGAGGAGCAGTACAACTCCACCTACCGCGTG
GTGAGCGTGCTGACCGTGCTGCACCAGGACTGGCTGAACGGCAAGGAGTACAAGTGCAAGGTGAGCAACAAGGCC
CTGCCCGCTCCCATCGAGAAGACCATCAGCAAGGCCAAGGGCCAGCCCCGGGAGCCTCAGGTGTACACCCTGCCC
CCCAGCCGCGACGAGCTGACCAAGAACCAGGTGAGCCTGACCTGCCTGGTGAAGGGCTTCTACCCCTCCGACATC
GCCGTGGAGTGGGAGAGCAACGGCCAGCCTGAGAACAACTACAAGACCACCCCTCCCGTGCTGGACAGCGACGGC
AGCTTCTTCCTGTACAGCAAGCTGACCGTGGACAAGTCCCGGTGGCAGCAGGGCAACGTGTTCAGCTGCAGCGTG
ATGCACGAGGCCCTGCACAACCACTACACCCAGAAGAGCCTGAGCCTGAGCCCCGGATAG

The DNA sequence of light chain of chimeric 16A

SEQ ID NO.:4, 159-16A-1-hLambda 2 LC [L2267]:
ATGTCCGTGCCTACCCAGGTGCTGGGACTGCTGCTGCTGTGGCTGACCGACGCCAGATGTCAGGCTGTTGTGACT
CAGGAATCTGCACTCACCACATCACCTGGTGAAACAGTCACACTCACTTGTCGCTCAAGTACTGGGGCTGTTATA
ACTAGTAACTATGCCAACTGGGTCCAAGAAAAACCAGATCATTTATTCACTGGTCTAATAGGTCGTACCTACAAC
CGAGTTCCAGGTGTTCCTGCCAGATTCTCAGGCTCCCTGATTGGAGACAAGGCTGCCCTCACCATCACAGGGGCA
CAGACTGAGGATGAGGCAATATATTTCTGTGCTCTATGGTACAGCAACCATTTCGTGTTCGGTGGAGGAACCAAA
CTGACTGTCCTAGGACAGCCTAAGGCCGCTCCTTCCGTGACCCTGTTCCCTCCATCCTCCGAGGAACTGCAGGCC
AACAAGGCCACCCTCGTGTGCCTGATCTCCGACTTCTACCCTGGCGCCGTGACCGTGGCCTGGAAGGCTGATAGC
TCTCCTGTGAAGGCCGGCGTGGAAACCACCACCCCTTCCAAGCAGTCCAACAACAAATACGCCGCCTCCTCCTAC
CTGTCCCTGACCCCTGAGCAGTGGAAGTCCCACCGGTCCTACAGCTGCCAAGTGACCCACGAGGGCTCCACCGTG
GAAAAGACCGTGGCTCCTACCGAGTGCTCCTGA

Fig. 3 (continued)

The humanness scores of humanized light chains

| Chain Name | Note | Full-length (Framework+CDR) Cutoff = 84 | Framework Only Cutoff = 88 |
|---|---|---|---|
| L2267 (Chimeric Parental) | Light chain | 62.34 | 70.95 |
| L2987 (VL1) | Regular humanized | 82.98 | 96.33 |
| L2988 (VL2) | Regular humanized | 78.63 | 90.57 |

The humanness scores of humanized light chains

| Chain Name | Note | Full-length (Framework+CDR) Cutoff = 79 | Framework Only Cutoff = 84 |
|---|---|---|---|
| H2267 (Chimeric Parental) | Parental | 63.62 | 69.31 |
| H2987 (VH1) | Regular humanized; 6 highlighted residues changed | 82.72 | 91.67 |
| H2988 (VH2) | Regular humanized:; 6 highlighted residues changed | 81.68 | 90.80 |
| H2989 (VH3) | Regular humanized; 5 highlighted residues changed | 80.22 | 88.62 |
| H2990 (VH4) | No change in highlighted residues | 76.59 | 84.25 |
| H2991 (VH5) | Balanced change; 3 highlighted residues changed | 79.40 | 87.53 |

Fig. 4

Amino acid and nucleotide sequences of humanized heavy chains

> H2987 (Humanized HC 1)
SEQ ID NO.:5
MDPKGSLSWRILLFLSLAFELSYGEVQLVESGGGLVQPGGSLRLSCAVSGIDFSRYWMSWVRQA
PGKGLEWVAEITPDSNTINYVPSVKGRFTISRDNAKNSLYLQMNSLRAEDTAVYYCASYYEGFAY
WGQGTLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCSVM
HEALHNHYTQKSLSLSPG**

SEQ ID NO.:6
ATGGACCCCAAGGGCAGCCTGAGCTGGAGAATCCTGCTGTTCCTGAGCCTGGCCTTCGAGC
TGAGCTACGGCGAAGTGCAGCTGGTGGAATCTGGCGGCGGACTGGTGCAGCCTGGCGGAT
CTCTGAGACTGTCCTGCGCCGTGTCCGGCATCGACTTCTCCCGGTACTGGATGTCCTGGGT
GCGACAGGCTCCTGGCAAGGGCCTGGAATGGGTGGCCGAGATCACCCCCGACTCCAACAC
CATCAACTACGTGCCCTCCGTGAAGGGCCGGTTCACCATCTCCAGAGACAACGCCAAGAAC
TCCCTGTACCTGCAGATGAACAGCCTGCGGGCCGAGGATACCGCCGTGTACTACTGCGCCT
CCTACTACGAGGGCTTCGCCTATTGGGGCCAGGGCACCCTCGTGACCGTGTCCTCTGCTAG
CACCAAGGGCCCCAGCGTGTTCCCTCTGGCCCCCAGCAGCAAGAGCACCAGCGGCGGAAC
CGCCGCCCTGGGCTGCCTGGTGAAGGACTACTTCCCCGAGCCCGTGACCGTGTCCTGGAA
CAGCGGCGCTCTGACCAGCGGAGTGCACACCTTCCCTGCCGTGCTGCAGAGCAGCGGCCT
GTACTCCCTGAGCAGCGTGGTGACCGTGCCCAGCAGCAGCCTGGGCACCCAGACCTACATC
TGCAACGTGAACCACAAGCCCTCCAACACCAAGGTGGACAAGAAGGTGGAGCCTAAGAGCT
GCGACAAGACCCACACCTGCCCTCCCTGCCCCGCCCCCGAGCTGCTGGGCGGACCCAGCG
TGTTCCTGTTCCCTCCCAAGCCCAAGGACACCCTGATGATCAGCCGCACCCCCGAGGTGAC
CTGCGTGGTGGTGGACGTGAGCCACGAGGACCCCGAGGTGAAGTTCAACTGGTACGTGGA
CGGCGTGGAGGTGCACAACGCCAAGACCAAGCCTCGGGAGGAGCAGTACAACTCCACCTA
CCGCGTGGTGAGCGTGCTGACCGTGCTGCACCAGGACTGGCTGAACGGCAAGGAGTACAA
GTGCAAGGTGAGCAACAAGGCCCTGCCCGCTCCCATCGAGAAGACCATCAGCAAGGCCAAG
GGCCAGCCCCGGGAGCCTCAGGTGTACACCCTGCCCCCCAGCCGCGACGAGCTGACCAAG
AACCAGGTGAGCCTGACCTGCCTGGTGAAGGGCTTCTACCCCTCCGACATCGCCGTGGAGT
GGGAGAGCAACGGCCAGCCTGAGAACAACTACAAGACCACCCCTCCCGTGCTGGACAGCG
ACGGCAGCTTCTTCCTGTACAGCAAGCTGACCGTGGACAAGTCCCGGTGGCAGCAGGGCAA
CGTGTTCAGCTGCAGCGTGATGCACGAGGCCCTGCACAACCACTACACCCAGAAGAGCCTG
AGCCTGAGCCCCGGATAGTAA

Variable region

Fig. 5

> H2988 (Humanized HC 2)

SEQ ID NO.:7

MDPKGSLSWRILLFLSLAFELSYG<mark>EVQLVESGGGLVQPGGSLRLSCAVSGIDFSRYWMSWVRQA</mark>
<mark>PGKGLEWVGEITPDSNTINYVPSVKGRFTISRDNAKNSLYLQMNSLRAEDTAVYYCASYYEGFAY</mark>
<mark>WGQGTLVTVSS</mark>ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCSVM
HEALHNHYTQKSLSLSPG**

SEQ ID NO.:8
ATGGACCCCAAGGGCAGCCTGAGCTGGAGAATCCTGCTGTTCCTGAGCCTGGCCTTCGAGC
TGAGCTACGGCGAAGTGCAGCTGGTGGAATCTGGCGGCGGACTGGTGCAGCCTGGCGGAT
CTCTGAGACTGTCCTGCGCCGTGTCCGGCATCGACTTCTCCCGGTACTGGATGTCCTGGGT
GCGACAGGCTCCTGGCAAGGGCCTGGAATGGGTGGGAGAGATCACCCCCGACTCCAACAC
CATCAACTACGTGCCCTCCGTGAAGGGCCGGTTCACCATCTCCAGAGACAACGCCAAGAAC
TCCCTGTACCTGCAGATGAACAGCCTGCGGGCCGAGGATACCGCCGTGTACTACTGCGCCT
CCTACTACGAGGGCTTCGCCTATTGGGGCCAGGGCACCCTCGTGACCGTGTCCTCTGCTAG
CACCAAGGGCCCCAGCGTGTTCCCTCTGGCCCCCAGCAGCAAGAGCACCAGCGGCGGAAC
CGCCGCCCTGGGCTGCCTGGTGAAGGACTACTTCCCCGAGCCCGTGACCGTGTCCTGGAA
CAGCGGCGCTCTGACCAGCGGAGTGCACACCTTCCCTGCCGTGCTGCAGAGCAGCGGCCT
GTACTCCCTGAGCAGCGTGGTGACCGTGCCCAGCAGCAGCCTGGGCACCCAGACCTACATC
TGCAACGTGAACCACAAGCCCTCCAACACCAAGGTGGACAAGAAGGTGGAGCCTAAGAGCT
GCGACAAGACCCACACCTGCCCTCCCTGCCCCGCCCCCGAGCTGCTGGGCGGACCCAGCG
TGTTCCTGTTCCCTCCCAAGCCCAAGGACACCCTGATGATCAGCCGCACCCCCGAGGTGAC
CTGCGTGGTGGTGGACGTGAGCCACGAGGACCCCGAGGTGAAGTTCAACTGGTACGTGGA
CGGCGTGGAGGTGCACAACGCCAAGACCAAGCCTCGGGAGGAGCAGTACAACTCCACCTA
CCGCGTGGTGAGCGTGCTGACCGTGCTGCACCAGGACTGGCTGAACGGCAAGGAGTACAA
GTGCAAGGTGAGCAACAAGGCCCTGCCCGCTCCCATCGAGAAGACCATCAGCAAGGCCAAG
GGCCAGCCCCGGGAGCCTCAGGTGTACACCCTGCCCCCCAGCCGCGACGAGCTGACCAAG
AACCAGGTGAGCCTGACCTGCCTGGTGAAGGGCTTCTACCCCTCCGACATCGCCGTGGAGT
GGGAGAGCAACGGCCAGCCTGAGAACAACTACAAGACCACCCCTCCCGTGCTGGACAGCG
ACGGCAGCTTCTTCCTGTACAGCAAGCTGACCGTGGACAAGTCCCGGTGGCAGCAGGGCAA
CGTGTTCAGCTGCAGCGTGATGCACGAGGCCCTGCACAACCACTACACCCAGAAGAGCCTG
AGCCTGAGCCCCGGATAGTAA

Fig. 5 (continued)

> H2989 (Humanized HC 3)

SEQ ID NO.:9

MDPKGSLSWRILLFLSLAFELSYG<u>EVKLVESGGGLVQPGGSLRLSCAVSGIDFSRYWMSWVRQA</u>
<u>PGKGLEWVGEITPDSNTINYVPSVKGRFTISRDNAKNSLYLQMNSLRAEDTAVYFCASYYEGFAY</u>
<u>WGQGTLVTVSS</u>ASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCSVM
HEALHNHYTQKSLSLSPG**

SEQ ID NO.:10

ATGGACCCCAAGGGCAGCCTGAGCTGGAGAATCCTGCTGTTCCTGAGCCTGGCCTTCGAGC
TGAGCTACGGCGAAGTGAAGCTGGTGGAATCTGGCGGCGGACTGGTGCAGCCTGGCGGAT
CTCTGAGACTGTCCTGCGCCGTGTCCGGCATCGACTTCTCCCGGTACTGGATGTCCTGGGT
GCGACAGGCTCCTGGCAAGGGCCTGGAATGGGTGGGAGAGATCACCCCCGACTCCAACAC
CATCAACTACGTGCCCTCCGTGAAGGGCCGGTTCACCATCTCCAGAGACAACGCCAAGAAC
TCCCTGTACCTGCAGATGAACAGCCTGCGGGCCGAGGATACCGCCGTGTACTTCTGCGCCT
CCTACTACGAGGGCTTCGCCTATTGGGGCCAGGGCACCCTCGTGACCGTGTCCTCTGCTAG
CACCAAGGGCCCCAGCGTGTTCCCTCTGGCCCCCAGCAGCAAGAGCACCAGCGGCGGAAC
CGCCGCCCTGGGCTGCCTGGTGAAGGACTACTTCCCCGAGCCCGTGACCGTGTCCTGGAA
CAGCGGCGCTCTGACCAGCGGAGTGCACACCTTCCCTGCCGTGCTGCAGAGCAGCGGCCT
GTACTCCCTGAGCAGCGTGGTGACCGTGCCCAGCAGCAGCCTGGGCACCCAGACCTACATC
TGCAACGTGAACCACAAGCCCTCCAACACCAAGGTGGACAAGAAGGTGGAGCCTAAGAGCT
GCGACAAGACCCACACCTGCCCTCCCTGCCCCGCCCCCGAGCTGCTGGGCGGACCCAGCG
TGTTCCTGTTCCCTCCCAAGCCCAAGGACACCCTGATGATCAGCCGCACCCCCGAGGTGAC
CTGCGTGGTGGTGGACGTGAGCCACGAGGACCCCGAGGTGAAGTTCAACTGGTACGTGGA
CGGCGTGGAGGTGCACAACGCCAAGACCAAGCCTCGGGAGGAGCAGTACAACTCCACCTA
CCGCGTGGTGAGCGTGCTGACCGTGCTGCACCAGGACTGGCTGAACGGCAAGGAGTACAA
GTGCAAGGTGAGCAACAAGGCCCTGCCCGCTCCCATCGAGAAGACCATCAGCAAGGCCAAG
GGCCAGCCCCGGGAGCCTCAGGTGTACACCCTGCCCCCCAGCCGCGACGAGCTGACCAAG
AACCAGGTGAGCCTGACCTGCCTGGTGAAGGGCTTCTACCCCTCCGACATCGCCGTGGAGT
GGGAGAGCAACGGCCAGCCTGAGAACAACTACAAGACCACCCCTCCCGTGCTGGACAGCG
ACGGCAGCTTCTTCCTGTACAGCAAGCTGACCGTGGACAAGTCCCGGTGGCAGCAGGGCAA
CGTGTTCAGCTGCAGCGTGATGCACGAGGCCCTGCACAACCACTACACCCAGAAGAGCCTG
AGCCTGAGCCCCGGATAGTAA

Fig. 5 (continued)

> H2990 (Humanized HC 4)

SEQ ID NO.:11

MDPKGSLSWRILLFLSLAFELSYGEVQLVESGGGLVQPGGFLRLSCVVSGIDFSRYWMSWVRQA
PGKGLEWVGEITPDSNTINYVPSVKGNFGISRDNAKNSLFLQMNSLRAEDTAVYFCASYYEGFAY
WGQGTLVTVSSASTKGPSVFPLAPSSKSTSGGTAALGCLVKDYFPEPVTVSWNSGALTSGVHTF
PAVLQSSGLYSLSSVVTVPSSSLGTQTYICNVNHKPSNTKVDKKVEPKSCDKTHTCPPCPAPELL
GGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSRDELTKNQVS
LTCLVKGFYPSDIAVEWESNGQPENNYKTTPPVLDSDGSFFLYSKLTVDKSRWQQGNVFSCSVM
HEALHNHYTQKSLSLSPG**

SEQ ID NO.:12

ATGGACCCCAAGGGCAGCCTGAGCTGGAGAATCCTGCTGTTCCTGAGCCTGGCCTTCGAGC
TGAGCTACGGCGAAGTGCAGCTGGTGGAATCTGGCGGCGGACTGGTGCAGCCTGGCGGCT
TTCTGAGACTGTCCTGCGTGGTGTCCGGCATCGACTTCTCCCGGTACTGGATGTCCTGGGT
GCGACAGGCTCCTGGCAAGGGCCTGGAATGGGTGGGAGAGATCACCCCCGACTCCAACAC
CATCAACTACGTGCCCTCCGTGAAGGGCAACTTCGGCATCTCCAGAGACAACGCCAAGAACT
CCCTGTTCCTGCAGATGAACAGCCTGCGGGCCGAGGATACCGCCGTGTACTTCTGCGCCTC
CTACTACGAGGGCTTCGCCTATTGGGGCCAGGGCACCCTCGTGACCGTGTCCTCTGCTAGC
ACCAAGGGCCCCAGCGTGTTCCCTCTGGCCCCCAGCAGCAAGAGCACCAGCGGCGGAACC
GCCGCCCTGGGCTGCCTGGTGAAGGACTACTTCCCCGAGCCCGTGACCGTGTCCTGGAAC
AGCGGCGCTCTGACCAGCGGAGTGCACACCTTCCCTGCCGTGCTGCAGAGCAGCGGCCTG
TACTCCCTGAGCAGCGTGGTGACCGTGCCCAGCAGCAGCCTGGGCACCCAGACCTACATCT
GCAACGTGAACCACAAGCCCTCCAACACCAAGGTGGACAAGAAGGTGGAGCCTAAGAGCTG
CGACAAGACCCACACCTGCCCTCCCTGCCCCGCCCCCGAGCTGCTGGGCGGACCCAGCGT
GTTCCTGTTCCCTCCCAAGCCCAAGGACACCCTGATGATCAGCCGCACCCCCGAGGTGACC
TGCGTGGTGGTGGACGTGAGCCACGAGGACCCCGAGGTGAAGTTCAACTGGTACGTGGAC
GGCGTGGAGGTGCACAACGCCAAGACCAAGCCTCGGGAGGAGCAGTACAACTCCACCTAC
CGCGTGGTGAGCGTGCTGACCGTGCTGCACCAGGACTGGCTGAACGGCAAGGAGTACAAG
TGCAAGGTGAGCAACAAGGCCCTGCCCGCTCCCATCGAGAAGACCATCAGCAAGGCCAAGG
GCCAGCCCCGGGAGCCTCAGGTGTACACCCTGCCCCCCAGCCGCGACGAGCTGACCAAGA
ACCAGGTGAGCCTGACCTGCCTGGTGAAGGGCTTCTACCCCTCCGACATCGCCGTGGAGTG
GGAGAGCAACGGCCAGCCTGAGAACAACTACAAGACCACCCCTCCCGTGCTGGACAGCGA
CGGCAGCTTCTTCCTGTACAGCAAGCTGACCGTGGACAAGTCCCGGTGGCAGCAGGGCAA
CGTGTTCAGCTGCAGCGTGATGCACGAGGCCCTGCACAACCACTACACCCAGAAGAGCCTG
AGCCTGAGCCCCGGATAGTAA

Fig. 5 (continued)

> H2991 (Humanized HC 5)

SEQ ID NO.:13

MDPKGSLSWRILLFLSLAFELSYGEVQLVESGGGLVQPGGSLRLSCVVSGIDFSRYWMSWVRQ
APGKGLEWVGEITPDSNTINYVPSVKGRFGISRDNAKNSLYLQMNSLRAEDTAVYFCASYYEGFA
YWGQGTLVTVSSASTKGPSVFPLAPSSKSTSGGTAALGCLVKDYFPEPVTVSWNSGALTSGVHT
FPAVLQSSGLYSLSSVVTVPSSSLGTQTYICNVNHKPSNTKVDKKVEPKSCDKTHTCPPCPAPEL
LGGPSVFLFPPKPKDTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQVYTLPPSRDELTKNQV
SLTCLVKGFYPSDIAVEWESNGQPENNYKTTPPVLDSDGSFFLYSKLTVDKSRWQQGNVFSCSV
MHEALHNHYTQKSLSLSPG**

SEQ ID NO.:14

ATGGACCCCAAGGGCAGCCTGAGCTGGAGAATCCTGCTGTTCCTGAGCCTGGCCTTCGAGC
TGAGCTACGGCGAAGTGCAGCTGGTGGAATCTGGCGGCGGACTGGTGCAGCCTGGCGGAT
CTCTGAGACTGTCCTGCGTGGTGTCCGGCATCGACTTCTCCCGGTACTGGATGTCCTGGGT
GCGACAGGCTCCTGGCAAGGGCCTGGAATGGGTGGGAGAGATCACCCCCGACTCCAACAC
CATCAACTACGTGCCCTCCGTGAAGGGCCGGTTCGGCATCTCCAGAGACAACGCCAAGAAC
TCCCTGTACCTGCAGATGAACAGCCTGCGGGCCGAGGATACCGCCGTGTACTTCTGCGCCT
CCTACTACGAGGGCTTCGCCTATTGGGGCCAGGGCACCCTCGTGACCGTGTCCTCTGCTAG
CACCAAGGGCCCCAGCGTGTTCCCTCTGGCCCCCAGCAGCAAGAGCACCAGCGGCGGAAC
CGCCGCCCTGGGCTGCCTGGTGAAGGACTACTTCCCCGAGCCCGTGACCGTGTCCTGGAA
CAGCGGCGCTCTGACCAGCGGAGTGCACACCTTCCCTGCCGTGCTGCAGAGCAGCGGCCT
GTACTCCCTGAGCAGCGTGGTGACCGTGCCCAGCAGCAGCCTGGGCACCCAGACCTACATC
TGCAACGTGAACCACAAGCCCTCCAACACCAAGGTGGACAAGAAGGTGGAGCCTAAGAGCT
GCGACAAGACCCACACCTGCCCTCCCTGCCCCGCCCCCGAGCTGCTGGGCGGACCCAGCG
TGTTCCTGTTCCCTCCCAAGCCCAAGGACACCCTGATGATCAGCCGCACCCCCGAGGTGAC
CTGCGTGGTGGTGGACGTGAGCCACGAGGACCCCGAGGTGAAGTTCAACTGGTACGTGGA
CGGCGTGGAGGTGCACAACGCCAAGACCAAGCCTCGGGAGGAGCAGTACAACTCCACCTA
CCGCGTGGTGAGCGTGCTGACCGTGCTGCACCAGGACTGGCTGAACGGCAAGGAGTACAA
GTGCAAGGTGAGCAACAAGGCCCTGCCCGCTCCCATCGAGAAGACCATCAGCAAGGCCAAG
GGCCAGCCCCGGGAGCCTCAGGTGTACACCCTGCCCCCCAGCCGCGACGAGCTGACCAAG
AACCAGGTGAGCCTGACCTGCCTGGTGAAGGGCTTCTACCCCTCCGACATCGCCGTGGAGT
GGGAGAGCAACGGCCAGCCTGAGAACAACTACAAGACCACCCCTCCCGTGCTGGACAGCG
ACGGCAGCTTCTTCCTGTACAGCAAGCTGACCGTGGACAAGTCCCGGTGGCAGCAGGGCAA
CGTGTTCAGCTGCAGCGTGATGCACGAGGCCCTGCACAACCACTACACCCAGAAGAGCCTG
AGCCTGAGCCCCGGATAGTAA

Fig.5 (continued)

Amino acid and nucleotide sequences of humanized light chains

> L2987 (Humanized LC 1)

SEQ ID NO.:15

MSVPTQVLGLLLLWLTDARCQAVVTQEPSLTVSPGGTVTLTCGSSTGAVITSNYANWFQQKPGQAP
RTLIGRTYNKVPWTPARFSGSLLGGKAALTLSGAQPEDEAEYYCALWYSNHFVFGGGTKLTVLGQP
KAAPSVTLFPPSSEELQANKATLVCLISDFYPGAVTVAWKADSSPVKAGVETTTPSKQSNNKYAASS
YLSLTPEQWKSHRSYSCQVTHEGSTVEKTVAPTECS**

SEQ ID NO.:16

ATGTCCGTGCCTACCCAGGTGCTGGGACTGCTGCTGCTGTGGCTGACCGACGCCAGATGTCAG
GCTGTCGTGACCCAGGAACCTTCCCTGACCGTGTCTCCTGGCGGCACCGTGACCCTGACCTGT
GGATCTTCTACCGGCGCTGTGATCACCTCCAACTACGCCAACTGGTTCCAGCAGAAGCCAGGC
CAGGCTCCTAGAACCCTGATCGGCAGAACCTACAACAAGGTGCCATGGACCCCTGCCCGGTTC
TCCGGATCTCTGCTGGGAGGAAAGGCCGCTCTGACCCTGTCTGGTGCCCAGCCTGAGGATGA
GGCCGAGTACTACTGCGCCCTGTGGTACTCCAACCACTTCGTGTTCGGCGGAGGCACCAAGCT
GACCGTGCTGGGACAGCCTAAGGCCGCTCCTTCCGTGACCCTGTTCCCTCCATCCTCCGAGGA
ACTGCAGGCCAACAAGGCCACCCTCGTGTGCCTGATCTCCGACTTCTACCCTGGCGCCGTGAC
CGTGGCCTGGAAGGCTGATAGCTCTCCTGTGAAGGCCGGCGTGGAAACCACCACCCCTTCCAA
GCAGTCCAACAACAAATACGCCGCCTCCTCCTACCTGTCCCTGACCCCTGAGCAGTGGAAGTC
CCACCGGTCCTACAGCTGCCAAGTGACCCACGAGGGCTCCACCGTGGAAAAGACCGTGGCTC
CTACCGAGTGCTCCTGATAA

> L2988 (Humanized LC2)

SEQ ID NO.:17

MSVPTQVLGLLLLWLTDARCQAVVTQEPSLTVSPGGTVTLTCGSSTGAVITSNYANWVQQKPGQAP
TGLIGRTYNKVPWTPARFSGSLLGDKAALTLSGAQPEDEAEYFCALWYSNHFVFGGGTKLTVLGQP
KAAPSVTLFPPSSEELQANKATLVCLISDFYPGAVTVAWKADSSPVKAGVETTTPSKQSNNKYAASS
YLSLTPEQWKSHRSYSCQVTHEGSTVEKTVAPTECS**

SEQ ID NO.:18

ATGTCCGTGCCTACCCAGGTGCTGGGACTGCTGCTGCTGTGGCTGACCGACGCCAGATGTCAG
GCTGTCGTGACCCAGGAACCTTCCCTGACCGTGTCTCCTGGCGGCACCGTGACCCTGACCTGT
GGATCTTCTACCGGCGCTGTGATCACCTCCAACTACGCCAACTGGGTGCAGCAGAAGCCAGGC
CAGGCTCCTACCGGCCTGATCGGCAGAACCTACAACAAGGTGCCATGGACCCCTGCCCGGTTC
TCCGGATCTCTGCTGGGCGATAAGGCCGCTCTGACCCTGTCTGGTGCCCAGCCTGAGGATGAG
GCCGAGTACTTCTGCGCCCTGTGGTACTCCAACCACTTCGTGTTCGGCGGAGGCACCAAGCTG
ACCGTGCTGGGACAGCCTAAGGCCGCTCCTTCCGTGACCCTGTTCCCTCCATCCTCCGAGGAA
CTGCAGGCCAACAAGGCCACCCTCGTGTGCCTGATCTCCGACTTCTACCCTGGCGCCGTGACC
GTGGCCTGGAAGGCTGATAGCTCTCCTGTGAAGGCCGGCGTGGAAACCACCACCCCTTCCAAG
CAGTCCAACAACAAATACGCCGCCTCCTCCTACCTGTCCCTGACCCCTGAGCAGTGGAAGTCC
CACCGGTCCTACAGCTGCCAAGTGACCCACGAGGGCTCCACCGTGGAAAAGACCGTGGCTCCT
ACCGAGTGCTCCTGATAA

Fig.5 (continued)

MONOCLONAL AND HUMANIZED ANTIBODIES TO A CANCER GLYCOPEPTIDE

FIELD OF THE INVENTION

The present invention relates to the field of biotechnology, particularly to the monoclonal and humanized antibodies or a functional fragment thereof against a cancer glycopeptide, and use of the same.

SEQUENCE LISTING

The Sequence Listing titled "REPLACEMENT 05/18/2022 SEQUENCE LISTING.TXT" created on May 18, 2022 having a size of 59,213 bytes is herein incorporated by reference.

BACKGROUND OF THE INVENTION

Cancer cells express abnormal glycoconjugates which are immune-suppressive biomacromolecules to subvert immune surveillance (FIG. 1). Abnormal glycosylated tumor mucins, such as MUC1, bind to BAX and activate anti-apoptotic pathway [1-2]. Furthermore, MUC1 glycans bind to signaling molecule of lymphocytes, Galectin-9, and inhibit the cytotoxic function of natural killer cells [3-4]. MUC1 is the highest expressed mucin in lung cancer, which has been widely studied in the treatment of lung cancer (small cell lung cancer and NSCLC). Our previous studies, including analysis of mRNA expression profiles of glycoproteins in 212 cases of lung cancer, confirmed that MUC1 is the preferred target for immunotherapy [5]. Previous studies by others also found that MUC1 protein bearing Tn and sialyl Tn sugar residues are expressed by breast, gastric, colon, pancreatic, and other cancer types [6-9].

It has been a challenge to generate highly specific antibodies against MUC1 glycopeptides. Glycans are poorly immunogenic due to their high hydrophilicity and lack of charges. The immunogenicity of the peptide part of a glycopeptide is far higher then their glycan part. Therefore antibodies which can recognize both the peptide and glycan parts are rare. Lakshminarayanan et al. found that 90% of antibodies from mice immunized by a glycopeptide can be inhibited by synthetic peptide part of the same glycopeptide. In other words, 90% of binding activities of antibodies induced by a glycopeptide vaccine are directed at peptide part [10].

MUC1 has been as a target for immunotherapy for decades. Most antibodies generated against MUC1 are induced by synthetic peptides containing the tandem repeat domain of MUC1, without glycan modification. These antibodies were found to be safe in phase I and II clinical trials [11]. However, no significant clinical benefits have been observed. It is believed that the antibody-dependent cell-mediated cytotoxicity is not sufficient to eliminate tumor in patients. Antibody-drug conjugates, chimeric antigen receptor (CAR) transduced T cells, have been reported to target several forms of MUC1 peptides or glycopeptides. huDS6-DM4 developed by Sanofi, recognizes a tumor-associated sialoglyco-epitope on MUC1, although the exact epitope sequence remains unclear (12). 5E5, a monoclonal antibody which binds to GalNAc (Tn) modified 60 mer tandem repeat sequence (13, 14), has shown great promise in the treatment of solid tumor (pancreatic cancer) when its VL and VH regions were used in the design of chimeric antigen receptor for T cell therapy (15).

For anti-glycopeptides antibodies with therapeutic value, they must have the high specificity to recognize tumor but not healthy tissues. While tumor tissues are known to express unique glycan structures such as Tn antigen (GalNAc), Sialyl Tn antigen (NeuAc alpha2,6 GalNAc), glycan structures are poorly immunogenic, and can not induce antibodies with high affinity. In order to obtain glycopeptide-specific antibodies which can recognize both glycans and polypeptides, we have screened mice immunized by tumor cells, and selected those few mice with higher serum antibody response to glycopeptide compared to non-glycosylated control peptide, and generated monoclonal antibodies specific to glycopeptides.

Murine antibodies must be humanized for therapeutic utilizations such as antibody-drugs, CAR (chimeric antigen receptor) T-cell therapy, in vivo antibody-based diagnostic reagents, etc. CDR (complimentary determination region) graft is the graft of mouse CDR of variable region, which recognizes antigen and determines the specificity of antibody. By grafting CDR of a mouse monoclonal antibody into variable region of a human antibody, and replacing human antibody's CDR, will gain the human antibody's binding to specific antigen, and reduces its immunogenicity in human.

Therefore, the inventors designed humanized light chains hVL1 and hVL2 sequence as well as humanized heavy chains hVH1, hVH2, hVH3, hVH4, hVH5 sequences for cVL gene and cVH gene of murine 16A. Humanized antibodies were designed by creating multiple hybrid sequences that fuse select parts of the parental antibody sequence with the human framework sequences. Using the 3D model, these humanized sequences were methodically analyzed by eye and computer modeling to isolate the sequences that would most likely retain antigen binding [16]. The goal was to maximize the amount of human sequence in the final humanized antibodies while retaining the original antibody specificity.

SUMMARY OF THE INVENTION

Objects of the present invention include providing the humanized and monoclonal antibodies or a functional fragment thereof against a cancer glycopeptide, and use of the same.

In a first aspect of the present invention, there is provided a humanized antibody or a functional fragment thereof, wherein the humanized antibody recognizes the MUC1 glycopeptide epitope, RPAPGS(GalNAc)TAPPAHG (SEQ ID NO.:34) on the surface of cancer cells.

The humanized antibodies are preferably monoclonal.

In a preferred embodiment, the humanized antibody functional or a fragment thereof comprises: a heavy chain sequence contains a variable region having CDRH1, CDRH2, and CDRH3, and the CDRH1 comprises an amino acid sequence set forth in SEQ ID NO: 28, the CDRH2 comprises the amino acid sequences set forth in SEQ ID NOS: 29, and the CDRH3 comprises an amino acid sequence set forth in SEQ ID NO: 30; and a light chain sequence contains a variable region having CDRL1, CDRL2, and CDRL3, and the CDRL1 comprises the amino acid sequences set forth in SEQ ID NO: 31, the CDRL2 comprises an amino acid sequence set forth in SEQ ID NO: 32, and the CDRL3 comprises an amino acid sequence set forth in SEQ ID NO: 33.

In another preferred embodiment, the humanized antibody or a functional fragment thereof comprises the variable region of the heavy chain sequence, the variable region comprises an amino acid sequence set forth in any one of SEQ ID NOs: 21-25.

In another preferred embodiment, the humanized antibody or a functional fragment thereof comprises the variable region of the light chain sequences, the variable region comprises an amino acid sequences set forth in SEQ ID NO: 26 or SEQ ID NO: 27.

In another preferred embodiment, the humanized antibody or a functional fragment thereof comprises humanized heavy chain sequences hVH1, hVH2, hVH3, hVH4, and hVH5 comprising an amino acid sequence set forth in SEQ ID NO: 5, SEQ ID NO: 7, SEQ ID NO: 9, SEQ ID NO: 11 and SEQ ID NO: 13, respectively.

In a yet preferred embodiment, the present invention provides the humanized antibody or a functional fragment thereof comprises humanized light chain sequences hVL1 and hVL2 comprising an amino acid sequences set forth in SEQ ID NO: 15 and SEQ ID NO: 17, respectively.

In a still preferred embodiment, there is provided a nucleotide sequence encoding the heavy chain hVH1, hVH2, hVH3, hVH4, and hVH5 of the humanized antibody or a functional fragment thereof as above mentioned, wherein the nucleotide sequence is depicted in SEQ ID NO: 6, SEQ ID NO: 8, SEQ ID NO: 10, SEQ ID NO: 12 and SEQ ID NO: 14, respectively. In a yet preferred embodiment, the present invention provides a nucleotide sequence encoding the light chain hVL1 and hVL2 of the humanized antibody or a functional fragment thereof as above mentioned, wherein the nucleotide sequence is depicted in SEQ ID NO: 16, and SEQ ID NO: 18.

In a second aspect of the present invention, there is provided a mouse-human chimeric antibody 16A or a functional fragment thereof, wherein the mouse-human chimeric antibody recognizes the MUC1 glycopeptide epitope, RPAPGS(GalNAc)TAPPAHG (SEQ ID NO.:34) on the surface of cancer cells.

In a preferred embodiment, the mouse-human chimeric antibody 16A or a functional fragment thereof comprises a heavy chain sequence cVH having an amino acid sequence depicted in SEQ ID NO: 1, and a light chain sequence cVL having an amino acid sequence depicted in SEQ ID NO: 2.

In another preferred embodiment, the present invention provides a nucleotide sequence encoding the heavy chain cVH of the mouse-human chimeric antibody 16A or a functional fragment thereof having the nucleotide sequence depicted in SEQ ID NO: 3. In a yet preferred embodiment, the present invention provides a nucleotide sequence encoding the light chain cVL of the mouse-human chimeric antibody 16A or a functional fragment thereof, wherein the gene has the nucleotide sequence depicted in SEQ ID NO: 4.

All the sequences are listed in Table 1 below.

In a third aspect of the present invention, there is provided an expression vector, wherein said expression vector comprises the nucleotide sequences the encoding the heavy chain hVH1, hVH2, hVH3, hVH4, and hVH5 of the humanized antibody as above mentioned, and/or the nucleotide sequences encoding the light chain hVL1 and hVL2 of the humanized antibody as above mentioned.

In a fourth aspect of the present invention, there is provided a host cell, wherein the cell comprises the expression vector as above mentioned, or has the nucleotide sequences as above mentioned integrated into its genome.

In a fifth aspect of the present invention, there is provided a pharmaceutical composition, comprises the mouse-human chimeric antibody 16A, which contains the VL and VH regions of mouse monoclonal antibody 16A and the constant region of human IgG1, or a functional fragment thereof and a pharmaceutically acceptable carrier.

In a sixth aspect of the present invention, there is provided a pharmaceutical composition, comprises the humanized antibody or a functional fragment thereof as above mentioned and a pharmaceutically acceptable carrier.

The present still provides the use of the humanized antibody or a functional fragment thereof as above mentioned in the prevention or treatment of the diseases such as cancers.

The present also provides the use of the mouse-human chimeric antibody 16A or a functional fragment thereof in the prevention or treatment of the diseases such as cancers.

The present still provides a method for preventing or treating cancers, wherein said method comprises administering to a subject in need an effective amount of the humanized antibody or a functional fragment thereof, or the mouse-human chimeric antibody 16A or a functional fragment thereof as above mentioned.

Other aspects of the present invention will be apparent to one skilled in the art in view of the present disclosure.

TABLE 1

| Sequences of the present invention | | | |
|---|---|---|---|
| Chain | name | Abbreviation | SEQ ID NO. |
| Amino acid sequence of chimeric 16A, heavy chain 159-16A-1-hIgG1 HC | H2267.ami | cVH.ami | SEQ ID NO.: 1 |
| Amino acid sequence of chimeric 16A, light chain 159-16A-1-hLambda 2 LC | L2267.ami | cVL.ami | SEQ ID NO.: 2 |
| Nucleotide sequence of chimeric 16A 159-16A-1-hIgG1 HC | H2267.nt | cVH.nt | SEQ ID NO.: 3 |
| Nucleotide sequence of chimeric 16A 159-16A-1-hLambda 2 LC | L2267.nt | cVL.nt | SEQ ID NO.: 4 |
| Amino acid sequence of humanized heavy chain H2987 | Humanized HC 1.ami | hVH1.ami | SEQ ID NO.: 5 |

TABLE 1-continued

Sequences of the present invention

| Chain | name | Abbreviation | SEQ ID NO. |
|---|---|---|---|
| Nucleotide sequence of humanized heavy chain H2987 | Humanized HC 1.nt | hVH1.nt | SEQ ID NO.: 6 |
| Amino acid sequence of humanized heavy chain H2988 | Humanized HC 2.ami | hVH2.ami | SEQ ID NO.: 7 |
| Nucleotide sequence of humanized heavy chain H2988 | Humanized HC 2.nt | hVH2.nt | SEQ ID NO.: 8 |
| Amino acid sequence of humanized heavy chain H2989 | Humanized HC 3.ami | hVH3.ami | SEQ ID NO.: 9 |
| Nucleotide sequence of humanized heavy chain H2989 | Humanized HC 3.nt | hVH3.nt | SEQ ID NO.: 10 |
| Amino acid sequence of humanized heavy chain H2990 | Humanized HC 4.ami | hVH4.ami | SEQ ID NO.: 11 |
| Nucleotide sequence of humanized heavy chain H2990 | Humanized HC 4.nt | hVH4.nt | SEQ ID NO.: 12 |
| Amino acid sequence of humanized heavy chain H2991 | Humanized HC 5.ami | hVH5.ami | SEQ ID NO.: 13 |
| Nucleotide sequence of humanized heavy chain H2991 | Humanized HC 5.nt | hVH5.nt | SEQ ID NO.: 14 |
| Amino acid sequence of humanized light chain L2987 | Humanized LC 1.ami | hVL1.ami | SEQ ID NO.: 15 |
| Nucleotide sequence of humanized light chain L2987 | Humanized LC 1.nt | hVL1.nt | SEQ ID NO.: 16 |
| Amino acid sequence of humanized light chain L2988 | Humanized LC2.ami | hVL2.ami | SEQ ID NO.: 17 |
| Nucleotide sequence of humanized light chain L2988 | Humanized LC2.nt | hVL2.nt | SEQ ID NO.: 18 |
| The amino acid sequence of variable region of heavy chain of chimeric 16A 159-16A-1-hIgG1 HC [VH2267] | VH2267.ami | [VH2267.ami] | SEQ ID NO.: 19 |
| The amino acid sequence of variable region of light chain of chimeric 16A 159-16A-1-hLambda 2 LC [VL2267] | VL2267.ami | [VL2267.ami] | SEQ ID NO.: 20 |
| Amino acid sequence of variable region of humanized heavy chain VH2987 (Humanized HC 1) | VH2987.ami | VH2987.ami | SEQ ID NO.: 21 |
| Amino acid sequence of variable region of humanized heavy chain VH2988 (Humanized HC 2) | VH2988.ami | VH2988.ami | SEQ ID NO. 22 |
| Amino acid sequence of variable region of humanized heavy chain VH2989 (Humanized HC 3) | VH2989.ami | VH2989.ami | SEQ ID NO.: 23 |
| Amino acid sequence of variable region of humanized heavy chain VH2990 (Humanized HC 4) | VH2990.ami | VH2990.ami | SEQ ID NO.: 24 |
| Amino acid sequence of variable region of humanized heavy chain VH2991 (Humanized HC 5) | VH2991.ami | VH2991.ami | SEQ ID NO.: 25 |

TABLE 1-continued

Sequences of the present invention

| Chain | name | Abbreviation | SEQ ID NO. |
|---|---|---|---|
| Amino acid sequence of variable region of humanized light chain VL2987 (Humanized LC 1) | VL2987.ami | VL2987.ami | SEQ ID NO.: 26 |
| Amino acid sequence of variable region of humanized light chain VL2988 (Humanized LC2) | VL2988.ami | VL2988.ami | SEQ ID NO.: 27 |
| Amino acid sequence of the Complimentary Determination Region of humanized heavy chain VH-CDR1 | VH-CDR1.ami | VH-CDR1.ami | SEQ ID NO.: 28 |
| Amino acid sequence of the Complimentary Determination Region of humanized heavy chains VH-CDR2 | VH-CDR2.ami | VH-CDR2.ami | SEQ ID NO.: 29 |
| Amino acid sequences of the Complimentary Determination Region of humanized heavy chain VH-CDR3 | VH-CDR3.ami | VH-CDR3.ami | SEQ ID NO.: 30 |
| Amino acid sequence of the Complimentary Determination Region of humanized heavy chain VL-CDR1 | VL-CDR1.ami | VL-CDR1.ami | SEQ ID NO.: 31 |
| Amino acid sequence of the Complimentary Determination Region of humanized heavy chains VL-CDR2 | VL-CDR2.ami | VL-CDR2.ami | SEQ ID NO.: 32 |
| Amino acid sequence of the Complimentary Determination Region of humanized heavy chain VL-CDR3 | VL-CDR3.ami | VL-CDR3.ami | SEQ ID NO.: 33 |

BRIEF DESCRIPTION OF THE DRAWINGS

FIG. 3 depicts amino acid and DNA sequences of 16A chimeric antibody. Each variable region is showed by dark area. The amino acid sequence of heavy chain of chimeric 16A, SEQ ID NO.:2, is shown. The amino acid sequence of the variable region of heavy chain of chimeric 16A, SEQ ID NO.:19, is shown. The amino acid sequence of the variable region of light chain chimeric 16A, SEQ ID NO.:20, is shown. The DNA sequence of heavy chain of chimeric 16A, SEQ ID NO.: 3, is shown. The DNA sequence of light chain of chimeric 16A, SEQ ID NO.:4, is shown.

FIG. 4 shows humanization degree of CDR grafted antibody.

FIG. 5 depicts amino acid and DNA sequence of humanized antibody. Each variable region is showed by dark area. The amino acid and nucleotide sequences of humanized heavy chains HC1, SEQ ID NO.:5 and SEQ ID NO.:6 respectively, are shown. The amino acid and nucleotide sequences of humanized heavy chains HC2, SEQ ID NO.:7 and SEQ ID NO.:8 respectively, are shown. The amino acid and nucleotide sequences of humanized heavy chains HC3, SEQ ID NO.:9 and SEQ ID NO.:10 respectively, are shown. The amino acid and nucleotide sequences of humanized heavy chains HC4, SEQ ID NO.:11 and SEQ ID NO.:12 respectively, are shown. The amino acid and nucleotide sequences of humanized heavy chains HC5, SEQ ID NO.:13 and SEQ ID NO.:14 respectively, are shown. The amino acid and nucleotide sequences of humanized light chains LC1 and LC2, SEQ ID NO.:15, SEQ ID NO.:16, SEQ ID NO.:17 and SEQ ID NO.:18 respectively, are shown.

DETAILED DESCRIPTION OF THE INVENTION

Figure 1:
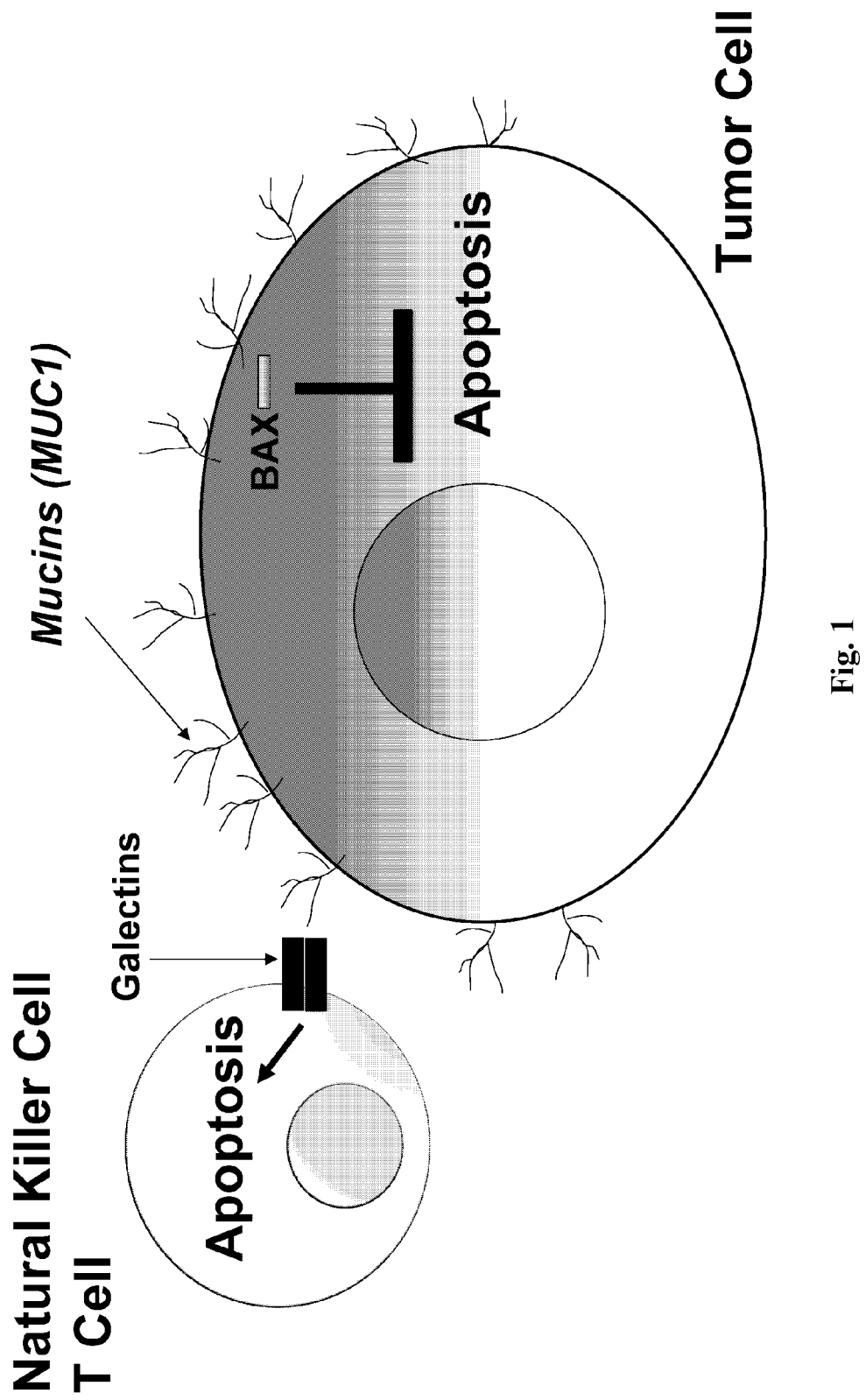
FIG. 1 illustrates tumor glycoconjugates promote tumor growth and subvert immune surveillance. Mucin MUC1 directly binds to BAX molecule and blocks apoptotic pathways of tumor cells. Mucin glycoproteins bind to galectins of NK cells and T cells, and induce the apoptosis of immune cells.
Figure 2:
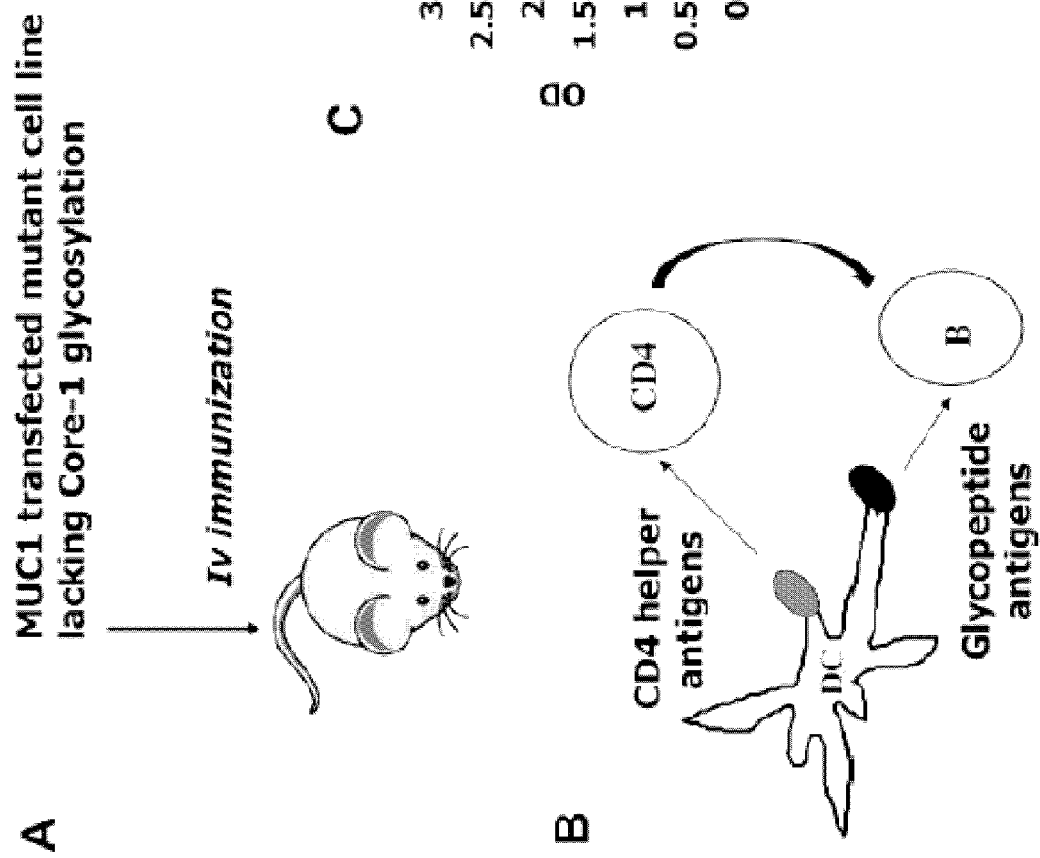
FIG. 2 illustrates generation of monoclonal antibodies by immunizing mice with xenogenic tumor cell lines lacking core-1 β3-galactosyltransferase activity. (A) C57B6 strain of mice were intravenously immunized by Jurkat cell line transfected by MUC1 gene; (B) MUC1 epitopes expressed on tumor cell surface stimulate B cells to produce antibodies. Tumor cell antigens provide CD4 T cell help to B cells. (C) Antibody responses toward glycopeptide can be detected by ELISA experiments. Monoclonal antibodies can be selected by using specific glycopeptides.

The following non-limiting examples are provided to further illustrate embodiments of the invention disclosed herein. It will be appreciated by those of skill in the art that the techniques disclosed in the examples that follow representative approaches that have been found to function well in the practice of the invention and thus can be considered to constitute examples of modes for its practice. However, those of skill in the art will, in light of the present disclosure, appreciate that many changes can be made in the specific embodiments that are disclosed and still obtain a like or similar result without departing from the spirit and scope of the invention.

Example 1. Cloning of cVL and cVH Genes of 16A Monoclonal Antibody

Total RNA was extracted from 16A murine hybridoma (from the University of Texas MD Anderson Cancer Center; reference: Int J Oncol 41(6):1977-84, 12/2012) by QIAGEN RNeasy Mini reagent (QIAGEN). cDNA was synthesized by SMARTer® (Switching Mechanism at the 5' end of RNA Template) RACE (Rapid Amplification of cDNA Ends) reagent (CLONTECH). The primer used for reverse transcription was Oligo-dT. cDNA was used as PCR template to clone cVH gene and cVL gene. Universal primer A mix (CLONTECH) and 5'-GGGRCCARKG GATAGACH-GATGG-3' (SEQ ID NO.:35) (designed according to the C segment of mouse IgG antibody heavy chain sequence) were used as cloning primers of cVH gene. Universal primer A mix (CLONTECH) and 5'-CTTCAGAGGA AGGGTG-GAAACAGG-3' (SEQ ID NO.:36) (designed according to the C segment of mouse IgG antibody light chain sequence) were used as cloning primers of cVL gene. cVH and cVL PCR fragments were sequenced by 3130XL ABI DNA sequencer.

Example 2. Design and Expression of Murine 16A Chimeric Antibody

The encoding gene of Chimeric 16A antibody is a hybrid structure wherein the murine 16A VH and VL gene fragments jointed to C region fragments of human IgG1. Amino acid and cDNA sequences of 16A chimeric antibody are as shown in FIG. 3. The VL and VH genes were synthesized by Sydlabs, MA. The synthesized genes were verified by DNA sequencing using 3130XL ABI DNA sequencer. Chimeric VL and chimeric VH genes were built into pcDNA3.1 expression vector (Invitrogen), as pcDNA3.1-chimeric VL and pcDNA3.1-chimeric-VH, respectively.

Example 3. Expression and Purification of Chimeric Antibody

HEK293 cells were cultured in serum-free media (DMEM, Life Technologies). pcDNA3.1-chimeric VL and pcDNA3.1-chimeric-VH were transiently transfected simultaneously by electroporation (Maxcyte). HEK293 cells were cultured for 5 additional days after electroporation, and culture supernatant was used in subsequent testing of antibody titer. Then culture supernatant was combined, and antibody was purified by Protein A affinity chromatography column (GE Healthcare).

Example 4. Design and Expression of Murine 16A Humanized (CDR Grafted) Antibody CDR of 16A antibody variable region directly determines the specificity of antibody. By grafting CDR of mouse monoclonal antibody into variable region of human antibody, we designed light chain hVL1 and hVL2 sequences, and heavy chain hVH1, hVH2, hVH3, hVH4 and hVH5 sequences. We hereby used hVL2 sequence in subsequent testing of antibody function.

Selection of the human antibody framework was based on BLAST (Basic Local Alignment Search Tool) search by mouse cVH and cVL amino acid sequences of 16A against the human hVH and hVL databases (IMGT®, the international ImMunoGeneTics information System®) respectively.

Humanized antibody was generated by grafting 16A CDR region to human antibody frame work. Furthermore, several amino acid sites were optimized by using computer 3D modeling. The aim was to obtain humanized sequences with the highest humanness score, while the specificity of 16A antibody is remained. The calculation method of humanized extent was according to Reference 16. Predicted humanness score was as shown in FIG. 4.

Amino acid and cDNA sequences of humanized 16 antibody were as shown in FIG. 5.

Figure 6:
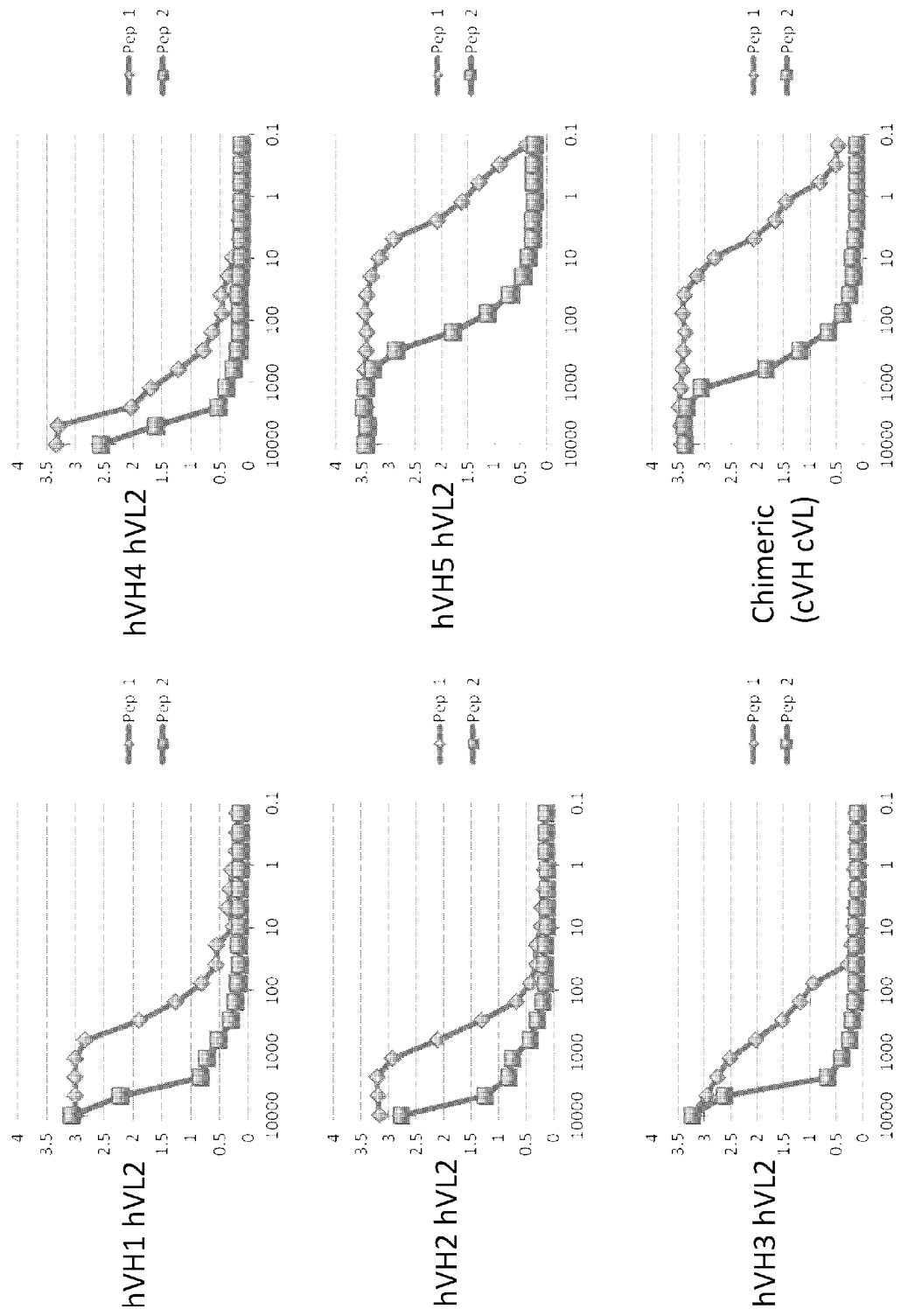
FIG. 6 illustrates specificity of chimeric and humanized antibodies as measured by ELISA. Pep1 is glycopeptide RPAPGS(GalNAc)TAPPAHG (SEQ ID NO.:34), Pep 2 is control polypeptide without glycosylation. Y-axis is the value of OD, X-axis is the concentrations of antibodies (ng/ml).

Example 5. Measurement of the Binding Activity of Monoclonal Antibodies to Glycopeptides ELISA plates were coated with streptavidin (1.5 µg/ml, Millipore) for overnight at 4 degree, and blocked by 1% BSA for 1 hour at room temperature. 2 µg/ml biotinylated glycopeptides (RPAPGS(GalNAc)TAPPAHG, (SEQ ID NO.:34) were attached to streptavidin coated plates. Serially diluted chimeric or humanized 16A antibodies (antibody concentrations as shown in FIG. 6) were incubated with glycopeptides. After washing three times with PBS 0.05% Tween®-20 (polyethylene glycol sorbitan monolaurate), the plates were then incubated with HRP-conjugated goat-anti-mouse secondary antibody. After three washes, the plates were incubated with DAB reagent. Non-glycosylated control peptide was used at the same concentrations to measure its binding to chimeric or humanized 16A antibodies.

Affinity of 16A chimeric antibody and humanized antibody for glycopeptides was higher than control polypeptides, particularly the hVH5hVL2. As shown in FIG. 6, strong binding to glycopeptide was found even at concentration of 10 ng/ml for the antibodies (OD=2.0). Whereas the antibody binding to control peptide (Peptide 2) was very low at 10 ng/ml antibody concentration (OD=ELISA background). The only difference between Peptide 1 and Peptide 2 is Peptide 2 had no sugar (GalNAc) modification.

Minimal concentration of chimeric and humanized antibodies to bind antigen RPAPGS(GalNAc)TAPPAHG (SEQ ID NO.:34), as determined by ELISA.

| Antibody | Minimum concentration of binding to glycopeptide (ng/ml) |
|---|---|
| Chimeric | 0.15 |
| hVH1hVL2 | 20 |
| hVH2hVL2 | 156 |
| hVH3hVL2 | 78 |
| hVH4hVL2 | 78 |
| hVH5hVL2 | 0.15 |

Figure 7:
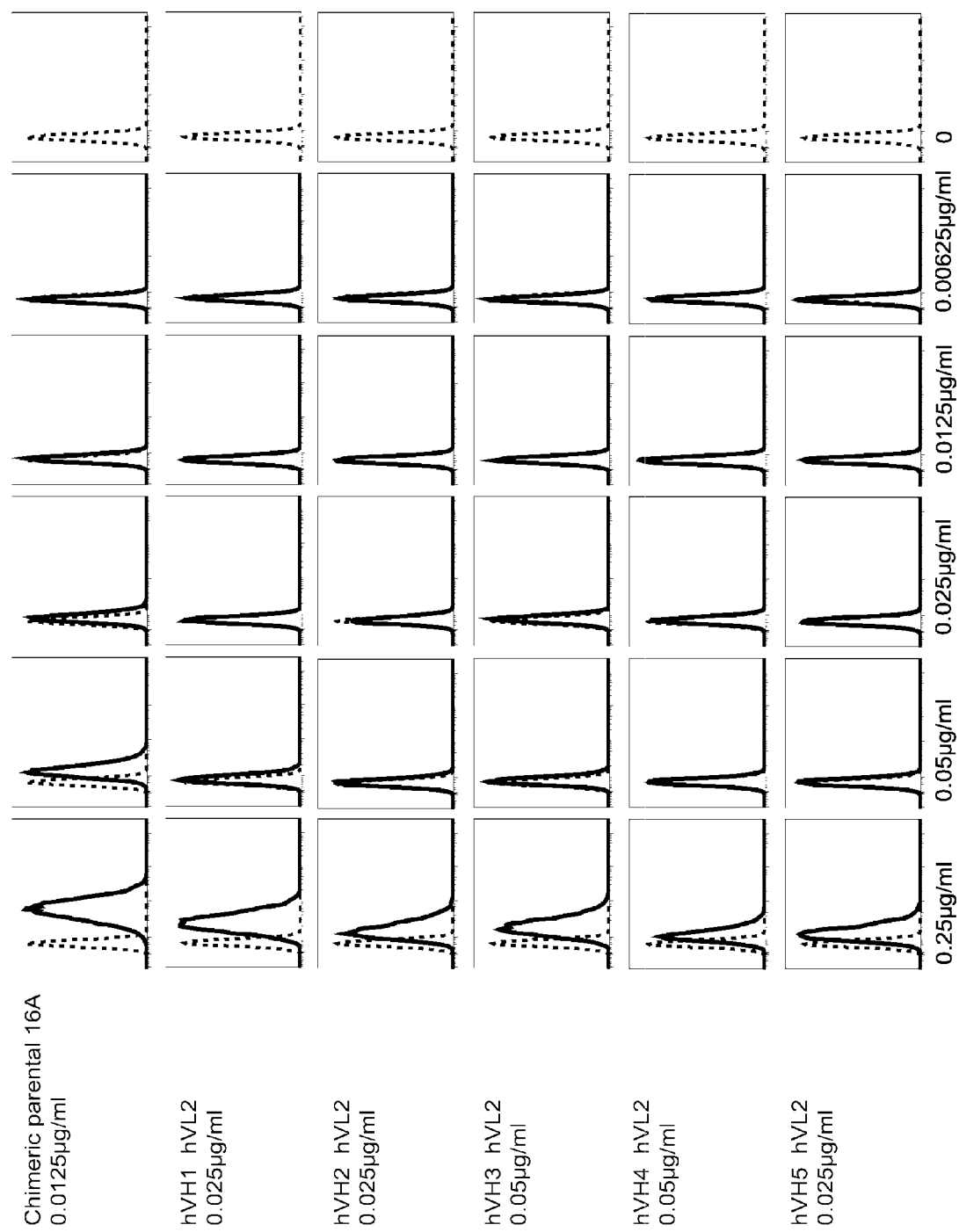
FIG. 7 illustrates binding of chimeric and humanized antibodies to lung cancer cell line H838. Lung cancer cell line H838 were stained with chimeric parental and humanized antibodies (hVH1hVL2, hVH2hVL2, hVH3hVL2, hVH4hVL2, and hVH5hVL2) with different concentrations. Solid line is the staining first by humanized antibodies and then fluorescence-labeled secondary antibody; dashed line is the staining by secondary antibody alone. The overlap of solid line and dashed line indicates the lowest staining concentration.
Figure 8:
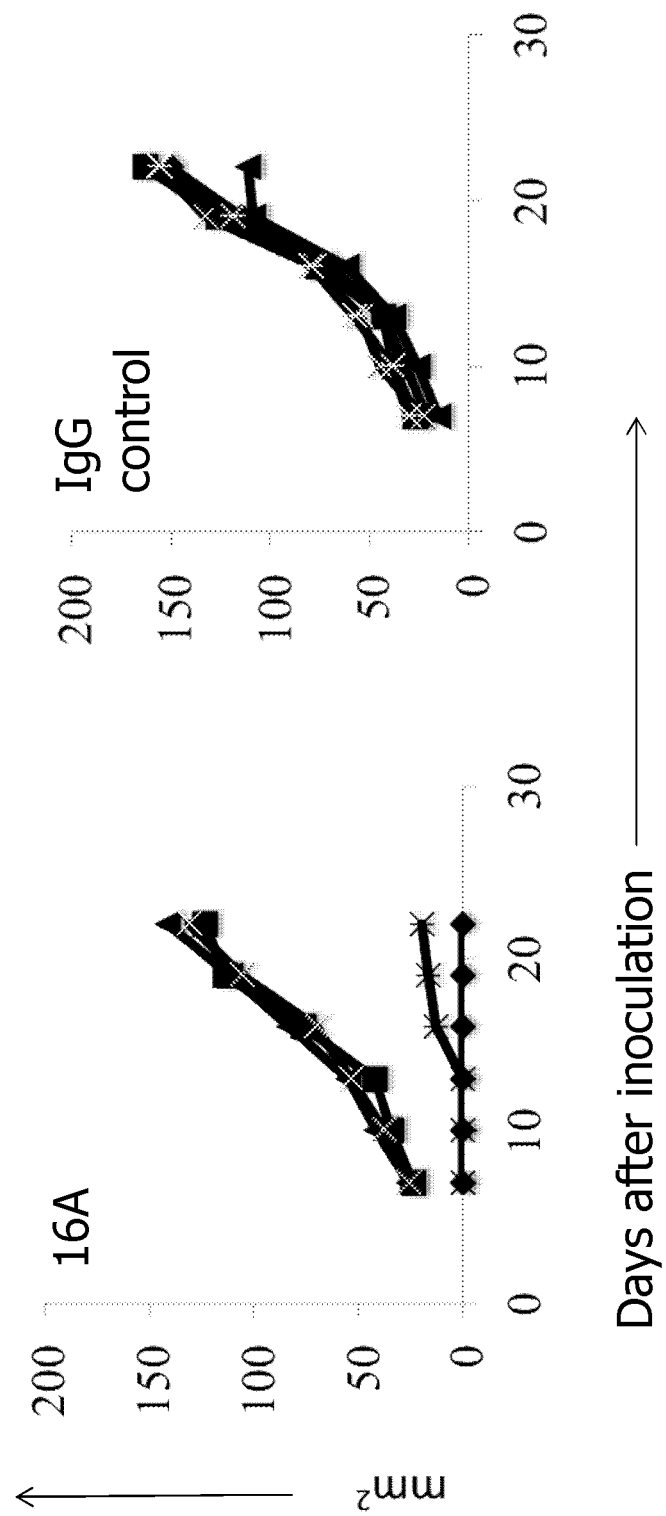
FIG. 8 illustrates the anti-tumor efficacy of 16A antibody. Left panel: 16A antibody drug group; Right panel: control IgG group. Each group contained 5 mice. The tumor growth curve of every mouse was presented. Data are representative of 3 independent experiments (The 16 A antibody inhibited the growth of tumor cell line).
Figure 9:
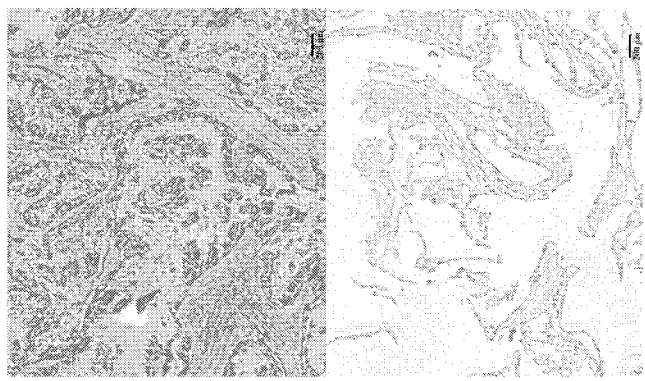
FIG. 9 illustrates the specific binding of 16A antibody to tissue section of a representative lung adenocarcinoma patient. Only tumor tissue is stained as positive, but not the peritumoral lung tissue.

Example 6. Measurement of Antibody Binding to Tumor Cells by Flow Cytometry Staining Lung cancer cell line H838 was obtained from the University of Texas M.D. Anderson Cancer Center. Cells were cultured in 10% RPMI 1640 medium. Different concentrations of chimeric antibody or humanized antibodies were used as primary antibody for staining, washed three times with PBS, then incubated with PE-conjugated mouse-anti-human IgG (BioLegend). The stained cells were analyzed by FACS Caliber flow cytometer (BD Biosciences, San Jose, Calif.). Staining results were as shown in FIG. 7.

Minimal concentration of chimeric and humanized antibodies to bind antigen, determined by cell surface staining of lung cancer cell line H838.

| Antibody | Minimum concentration of binding to lung cancer cell line H838 (µg/ml) |
|---|---|
| Chimeric | 0.0125 |
| hVH1hVL2 | 0.025 |
| hVH2hVL2 | 0.025 |
| hVH3hVL2 | 0.025 |
| hVH4hVL2 | 0.05 |
| hVH5hVL2 | 0.025 |

Example 7. Antitumor Efficacy of 16A Monoclonal Antibody

C3H mice (Jackson Laboratory, ME) were inoculated with Ag104-MUC1 cell line, a mouse fibrosarcoma cell line stably transfected by MUC1 gene (9). 6-week old C3H mice were inoculated with 2 million tumor cells subcutaneously. 100 micrograms of 16A antibody were administered by intraperitoneal injection at the same day of tumor inoculation. 16A antibody drug was given at 100 microgram per mouse every 3 days. Control mouse IgG antibody (from Southern Biotech, AL) was used to treat the tumor-bearing mice in the control group. The perpendicular diameters of tumor were measured and the tumor area was used to represent tumor burden. In mice treated by 16A monoclonal antibody, the tumor growth is significantly inhibited.

Example 8. Specific Binding of 16A Antibody to Cancer but not Peritumoral Tissue Immunohistochemistry was performed as previously described (9). Briefly, 5-µm paraffin-fixed tissue sections were deparaffinized in xylene and rehydrated through using a gradient of alcohol (100, 95 to 80%, Sigma, St. Louis, Mo.). Antigen retrieval was carried out for 30 min using PT Module (Lab Vision Corp., USA) in tris(hydroxyethyl) aminomethane-EDTA buffer (pH 9.0). After cooling down, the slides were thoroughly washed in distilled water and washed three times in 1× phosphate-buffered saline (PBS), 2 min each. Endogenous peroxidase activity was quenched by immersion in 3% hydrogen peroxide (Sigma), then in methanol for 10 min at room temperature followed by rinsing for 2 min in 1×PBS three times. Nonspecific binding of the primary antibody was blocked by incubating the sections with 10% normal horse serum for 30 min at room temperature. Sections were then incubated with primary anti-16A monoclonal antibody at 4° C. overnight, at 1 µg/ml concentration.

The second day, after washing three times in 1×PBS (2 min each), the slides were incubated with secondary anti-mouse IgG-biotin antibody (1:200, Vectastain® Elite ABC kit (an avidin/biotin based peroxidase system); Vector laboratories, CA, USA) at room temperature for 1 h and rinsed in 1×PBS three times (2 min each). After another 1-h incubation with the avidin-biotin peroxidase complex (1:100, Vectastain® Elite ABC Kit; Vector Laboratories, CA, USA) and repeated washing steps with 1×PBS, visualization was performed with the chromogen 3,3'-diaminobenzidine (DAB, Dako, Carpinteria, Calif., USA). The slides were counterstained with hematoxylin and coverslipped with PerMount. Sections of Jurkat-pcDNA-IRES-eGFP-MUC1 and Jurkat-pcDNA-IRES-eGFP were used as positive and negative controls, respectively. Isotype IgG and omission of the primary antibody were used as negative controls for staining.

All references cited in the present disclosure are hereby incorporated herein by reference as if each was individually incorporated herein by reference. In addition, it is understood that those skilled in the art will, in light of the teaching described hereinabove, make various changes and modifications to the present invention without departing from the spirit of the present invention, and these equivalents are deemed to fall within the scope of the present invention as defined in the appended claims.

REFERENCES

1. Ahmad R, Alam M, Rajabi H, Kufe D. (2012) The MUC1-C oncoprotein binds to the BH3 domain of the pro-apoptotic BAX protein and blocks BAX function. J Biol Chem. 287 (25):20866-75.
2. Xu X, Wells A, Padilla M T, et al. (2014) A signaling pathway consisting of miR-551b, catalase and MUC1 contributes to acquired apoptosis resistance and chemoresistance. Carcinogenesis. 35(11):2457-66.

3. Zhang K, Sikut R, Hansson G C. (1997) A MUC1 mucin secreted from a colon carcinoma cell line inhibits target cell lysis by natural killer cells. Cell Immunol. 176(2): 158-65.
4. Moreno M, Bontkes H J, Scheper R J, et al. (2007) High level of MUC1 in serum of ovarian and breast cancer patients inhibits huHMFG-1 dependent cell-mediated cytotoxicity (ADCC). Cancer Lett. 257(1):47-55.
5. Qu J, Yu H, Li F, Zhang C, Trad A, Brooks C, Zhang B, Gong T, Guo Z, Li Y, Ragupathi G, Lou Y, Hwu P, Huang W, Zhou D. Molecular basis of antibody binding to mucin glycopeptides in lung cancer. Int J Oncol. 2016 February; 48(2):587-94.
6. Devine P L, Birrell G W, Quin R J, et al. (1995) Monoclonal antibodies recognising sialyl-Tn: production and application to immunochemistry. Dis Markers. 12(3): 175-86.
7. Longenecker B M, Willans D J, MacLean G D, et al. (1987) Monoclonal antibodies and synthetic tumor-associated glycoconjugates in the study of the expression of Thomsen-Friedenreich-like and Tn-like antigens on human cancers. J Natl Cancer Inst. 78(3): 489-96.
8. Nguyen P L, Niehans G A, Cherwitz D L, et al. (1996) Membrane-bound (MUC1) and secretory (MUC2, MUC3, and MUC4) mucin gene expression in human lung cancer. Tumour Biol. 17(3):176-92.
9. Song W, Delyria E S, Chen J, Huang W, Lee J S, Mittendorf E A, Ibrahim N, Radvanyi LG, Li Y, Lu H, Xu H, Shi Y, Wang L X, Ross J A, Rodrigues S P, Almeida I C, Yang X, Qu J, Schocker N S, Michael K, Zhou D*. MUC1 glycopeptide epitopes predicted by computational glycomics. Int J Oncol 41(6):1977-84, 12/2012.
10. Lakshminarayanan V, Thompson P, Wolfert M A, Buskas T, Bradley J M, Pathangey L B, Madsen C S, Cohen P A, Gendler S J, et al.: Immune recognition of tumor-associated mucin MUC1 is achieved by a fully synthetic aberrantly glycosylated MUC1 tripartite vaccine. Proc Natl Acad Sci USA 109(1):261-266, 2012.
11. Ibrahim N K, Yariz K O, Bondarenko I, Manikhas A, Semiglazov V, Alyasova A, Komisarenko V, Shparyk Y, Murray J L, Jones D, Senderovich S, Chau A, Erlandsson F, Acton G, Pegram M. Randomized phase II trial of letrozole plus anti-MUC1 antibody AS1402 in hormone receptor-positive locally advanced or metastatic breast cancer. Clin Cancer Res. 2011 Nov. 1; 17(21):6822-30.
12. Sylvie ASSADOURIAN, Dominique MERY-MIGNARD. Use of anti-muc1 maytansinoid immunoconjugate antibody for the treatment of solid tumors. WO 2015014879 A1
13. Sorensen A L, Reis C A, Tarp M A, Mandel U, Ramachandran K, Sankaranarayanan V, Schwientek T, Graham R, Taylor-Papadimitriou J, Hollingsworth M A, Burchell J, Clausen H. Chemoenzymatically synthesized multimeric Tn/STn MUC1 glycopeptides elicit cancer-specific anti-MUC1 antibody responses and override tolerance. Glycobiology. 2006 February; 16(2):96-107
14. Henrik Clausen, Joy Burchell, Ulla Mandel, Anne Louise Sorensen, Mads Agervig Tarp, Joyce Taylor-Papadimitriou. Generation of a cancer-specific immune response toward MUC1 and cancer specific MUC1 antibodies. U.S. Pat. No. 8,440,798 B2
15. Posey A D Jr, Schwab R D, Boesteanu A C, Steentoft C, Mandel U, Engels B, Stone J D, Madsen T D, Schreiber K, Haines K M, Cogdill A P, Chen T J, Song D, Scholler J, Kranz D M, Feldman M D, Young R, Keith B, Schreiber H, Clausen H, Johnson L A, June C H. Engineered CAR T Cells Targeting the Cancer-Associated Tn-Glycoform of the Membrane Mucin MUC1 Control Adenocarcinoma. Immunity. 2016 Jun. 21; 44(6):1444-54.
16. Gao, S. H., Huang, K., Tu, H., and Adler, A. S. 2013. Monoclonal antibody humanness score and its applications. BMC Biotechnology, 13:55.

What is claimed is:

1. A humanized antibody or a functional fragment thereof, wherein the humanized antibody comprises: a heavy chain sequence that contains a variable region comprising CDRH1, CDRH2, and CDRH3, and the CDRH1 comprises an amino acid sequence set forth in SEQ ID NO: 28, the CDRH2 comprises the amino acid sequence set forth in SEQ ID NO: 29, and the CDRH3 comprises an amino acid sequence set forth in SEQ ID NO: 30;

a light chain sequence that contains a variable region comprising CDRL1, CDRL2, and CDRL3, and the CDRL1 comprises the amino acid sequence set forth in SEQ ID NO: 31, the CDRL2 comprises an amino acid sequence set forth in SEQ ID NO: 32, and the CDRL3 comprises an amino acid sequence set forth in SEQ ID NO: 33, wherein the humanized antibody or a functional fragment thereof specifically binds the MUC1 glycopeptide epitope RPAPGS(GalNAc)TAPPAHG comprising an amino acid sequence set forth in SEQ ID NO.:34 on the surface of cancer cells; and wherein the humanized antibody comprises the variable region of the heavy chain sequence comprising an amino acid sequence set forth in any one of SEQ ID NOs: 21-25.

2. The humanized antibody or a functional fragment thereof according to claim 1, wherein the humanized antibody comprises the variable region of the light chain sequence comprising an amino acid sequence set forth in SEQ ID NO: 26 or SEQ ID NO: 27.

3. The humanized antibody or a functional fragment thereof according to claim 1, wherein the humanized antibody comprises the heavy chain sequence comprising an amino acid sequence set forth in any one of SEQ ID NO: 5, SEQ ID NO: 7, SEQ ID NO: 9, SEQ ID NO: 11 or SEQ ID NO: 13.

4. The humanized antibody or a functional fragment thereof according to claim 1, wherein the humanized antibody comprises the light chain sequence comprising an amino acid sequence set forth in SEQ ID NO: 15 or SEQ ID NO: 17.

5. A mouse-human chimeric antibody or a functional fragment thereof, wherein the mouse-human chimeric antibody comprises a variable region of heavy chain comprising an amino acid sequence set forth in SEQ ID NO: 19, and a variable region of light chain comprising an amino acid sequence set forth in SEQ ID NO: 20, and the constant region of human IgG1, wherein the mouse-human chimeric antibody or a functional fragment thereof specifically binds the MUC1 glycopeptide epitope RPAPGS(GalNAc)TAPPAHG comprising an amino acid sequence set forth in SEQ ID NO.:34 on the surface of cancer cells; and
  wherein the mouse-human chimeric antibody comprises a heavy chain sequence comprising an amino acid sequence set forth in SEQ ID NO: 1, and a light chain sequence comprising an amino acid sequence set forth in SEQ ID NO: 2.

6. A nucleotide sequence encoding the heavy chain of the humanized antibody or a functional fragment thereof according to claim 1, wherein the nucleotide sequence is set forth in SEQ ID NO: 6, SEQ ID NO: 8, SEQ ID NO: 10, SEQ ID NO: 12 or SEQ ID NO: 14.

7. A nucleotide sequence encoding the light chain of the humanized antibody or a functional fragment thereof according to claim 1, wherein the nucleotide sequence is set forth in SEQ ID NO: 16 or SEQ ID NO: 18.

8. An expression vector, wherein said expression vector comprises the sequence according to claim 7.

9. A host cell, wherein said host cell comprises the expression vector according to claim 8.

10. An expression vector, wherein said expression vector comprises the sequence according to claim 6.

11. A host cell, wherein the cell comprises the expression vector according to claim 10.

12. A pharmaceutical composition comprising the humanized antibody or a functional fragment thereof according to claim 1.

13. A method for treating cancers expressing the MUC1 glycopeptide epitope RPAPGS(GalNAc)TAPPAHG comprising an amino acid sequence set forth in SEQ ID NO.:34 on the surface of cancer cells, wherein said method comprises administering to a subject in need thereof, an effective amount of the humanized antibody or a functional fragment thereof according to claim 1 as therapeutic for the treatment of the cancers.

\* \* \* \* \*

SEQUENCE LISTING

```
<160> NUMBER OF SEQ ID NOS: 36

<210> SEQ ID NO 1
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Lys Leu His Gln Ser Gly
            20                  25                  30

Gly Gly Leu Val Gln Pro Gly Gly Phe Leu Lys Ile Ser Cys Val Val
        35                  40                  45

Ser Gly Ile Asp Phe Ser Arg Tyr Trp Met Ser Trp Val Arg Arg Ala
    50                  55                  60

Pro Gly Lys Gly Leu Glu Trp Ile Gly Glu Ile Thr Pro Asp Ser Asn
65                  70                  75                  80

Thr Ile Asn Tyr Val Pro Ser Leu Lys Asp Asn Phe Gly Ile Ser Arg
                85                  90                  95

Asp Asn Ala Lys Asn Thr Leu Phe Leu Gln Met Thr Lys Val Arg Ser
            100                 105                 110
```

Glu Asp Thr Ala Leu Tyr Phe Cys Ala Ser Tyr Tyr Glu Gly Phe Ala
            115                 120                 125

Tyr Trp Gly Gln Gly Thr Leu Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
        180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly
465

<210> SEQ ID NO 2
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Met Ser Val Pro Thr Gln Val Leu Gly Leu Leu Leu Trp Leu Thr
1               5                   10                  15

Asp Ala Arg Cys Gln Ala Val Val Thr Gln Glu Ser Ala Leu Thr Thr
            20                  25                  30

Ser Pro Gly Glu Thr Val Thr Leu Thr Cys Arg Ser Ser Thr Gly Ala
        35                  40                  45

Val Ile Thr Ser Asn Tyr Ala Asn Trp Val Gln Glu Lys Pro Asp His
    50                  55                  60

Leu Phe Thr Gly Leu Ile Gly Arg Thr Tyr Asn Arg Val Pro Gly Val
65                  70                  75                  80

Pro Ala Arg Phe Ser Gly Ser Leu Ile Gly Asp Lys Ala Ala Leu Thr
                85                  90                  95

Ile Thr Gly Ala Gln Thr Glu Asp Glu Ala Ile Tyr Phe Cys Ala Leu
            100                 105                 110

Trp Tyr Ser Asn His Phe Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 3
<211> LENGTH: 1410
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atggacccca agggcagcct gagctggaga atcctgctgt tcctgagcct ggccttcgag      60
ctgagctacg cgaggtgaa gcttcaccag tctggaggtg gcctggtgca gcctggagga     120
ttcctgaaaa tctcctgtgt agtctcagga atcgatttta gtagatactg gatgagttgg     180
gttcggcggg ctccagggaa aggactagaa tggattggag aaattactcc agatagcaat     240
acaataaact atgtaccatc tctaaaggat aatttcggca tctccagaga caacgccaaa     300
aatacgctgt tcctgcaaat gaccaaagtg agatctgagg acacagccct ttatttctgt     360
gcatcctact acgagggatt tgcttactgg ggccaaggga ctctggtcac tgtctctgca     420
gctagcacca agggccccag cgtgttccct ctggccccca gcagcaagag caccagcggc     480
ggaaccgccg ccctgggctg cctggtgaag gactacttcc ccgagcccgt gaccgtgtcc     540
tggaacagcg gcgctctgac cagcggagtg cacaccttcc ctgccgtgct gcagagcagc     600
ggcctgtact ccctgagcag cgtggtgacc gtgcccagca gcagcctggg cacccagacc     660

```
tacatctgca acgtgaacca caagccctcc aacaccaagg tggacaagaa ggtggagcct    720
aagagctgcg acaagaccca cacctgccct ccctgccccg cccccgagct gctgggcgga    780
cccagcgtgt tcctgttccc tcccaagccc aaggacaccc tgatgatcag ccgcaccccc    840
gaggtgacct gcgtggtggt ggacgtgagc cacgaggacc ccgaggtgaa gttcaactgg    900
tacgtggacg gcgtggaggt gcacaacgcc aagaccaagc ctcgggagga gcagtacaac    960
tccacctacc gcgtggtgag cgtgctgacc gtgctgcacc aggactggct gaacggcaag   1020
gagtacaagt gcaaggtgag caacaaggcc ctgcccgctc ccatcgagaa gaccatcagc   1080
aaggccaagg gccagccccg ggagcctcag gtgtacaccc tgcccccag ccgcgacgag    1140 ctgaccaaga accaggtgag cctgacctgc ctggtgaagg gcttctaccc ctccgacatc   1200
gccgtggagt gggagagcaa cggccagcct gagaacaact acaagaccac ccctcccgtg   1260
ctggacagcg acggcagctt cttcctgtac agcaagctga ccgtggacaa gtcccggtgg   1320
cagcagggca acgtgttcag ctgcagcgtg atgcacgagg ccctgcacaa ccactacacc   1380
cagaagagcc tgagcctgag ccccggatag                                    1410
```

```
<210> SEQ ID NO 4
<211> LENGTH: 708
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 4
atgtccgtgc ctacccaggt gctgggactg ctgctgctgt ggctgaccga cgccagatgt     60
caggctgttg tgactcagga atctgcactc accacatcac ctggtgaaac agtcacactc    120
acttgtcgct caagtactgg ggctgttata actagtaact atgccaactg gtccaagaa     180 aaaccagatc atttattcac tggtctaata ggtcgtacct acaaccgagt tccaggtgtt    240
cctgccagat tctcaggctc cctgattgga gacaaggctg ccctcaccat cacaggggca    300
cagactgagg atgaggcaat atatttctgt gctctatggt acagcaacca tttcgtgttc    360
ggtggaggaa ccaaactgac tgtcctagga cagcctaagg ccgctccttc cgtgaccctg    420
ttccctccat cctccgagga actgcaggcc aacaaggcca ccctcgtgtg cctgatctcc    480
gacttctacc ctggcgccgt gaccgtggcc tggaaggctg atagctctcc tgtgaaggcc    540
ggcgtggaaa ccaccacccc ttccaagcag tccaacaaca atacgccgc ctcctcctac    600 ctgtccctga cccctgagca gtggaagtcc caccggtcct cagctgcca agtgacccac    660 gagggctcca ccgtggaaaa gaccgtggct cctaccgagt gctcctga              708
```

```
<210> SEQ ID NO 5
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 5

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30
```

-continued

Gly Gly Leu Val Gln Pro Gly Gly Ser Leu Arg Leu Ser Cys Ala Val
                35                  40                  45

Ser Gly Ile Asp Phe Ser Arg Tyr Trp Met Ser Trp Val Arg Gln Ala
    50                  55                  60

Pro Gly Lys Gly Leu Glu Trp Val Ala Glu Ile Thr Pro Asp Ser Asn
65                  70                  75                  80

Thr Ile Asn Tyr Val Pro Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Tyr Cys Ala Ser Tyr Tyr Glu Gly Phe Ala
            115                 120                 125

Tyr Trp Gly Gln Gly Thr Leu Val Thr Val Ser Ser Ala Ser Thr Lys
        130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu

Ser Leu Ser Pro Gly
465

<210> SEQ ID NO 6
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 6

```
atggacccca agggcagcct gagctggaga atcctgctgt tcctgagcct ggccttcgag      60
ctgagctacg gcgaagtgca gctggtggaa tctggcggcg gactggtgca gcctggcgga     120
tctctgagac tgtcctgcgc cgtgtccggc atcgacttct cccggtactg gatgtcctgg     180
gtgcgacagg ctcctggcaa gggcctggaa tgggtggccg agatcacccc cgactccaac     240
accatcaact acgtgccctc cgtgaagggc cggttcacca tctccagaga caacgccaag     300
aactccctgt acctgcagat gaacagcctg cgggccgagg ataccgccgt gtactactgc     360
gcctcctact acgagggctt cgcctattgg ggccagggca cctcgtgac cgtgtcctct     420
gctagcacca agggcccag cgtgttccct ctggccccca gcagcaagag caccagcggc     480
ggaaccgccg ccctgggctg cctggtgaag gactacttcc ccgagcccgt gaccgtgtcc     540
tggaacagcg gcgctctgac cagcggagtg cacaccttcc ctgccgtgct gcagagcagc     600
ggcctgtact ccctgagcag cgtggtgacc gtgcccagca gcagcctggg cacccagacc     660
tacatctgca acgtgaacca caagccctcc aacaccaagg tggacaagaa ggtggagcct     720
aagagctgcg acaagaccca cacctgccct cctgccccg ccccgagct gctgggcgga     780
cccagcgtgt tcctgttccc tcccaagccc aaggacaccc tgatgatcag ccgcacccc     840
gaggtgacct gcgtggtggt ggacgtgagc cacgaggacc ccgaggtgaa gttcaactgg     900
tacgtggacg gcgtggaggt gcacaacgcc aagaccaagc ctcgggagga gcagtacaac     960
tccacctacc gcgtggtgag cgtgctgacc gtgctgcacc aggactggct gaacggcaag    1020
gagtacaagt gcaaggtgag caacaaggcc ctgcccgctc ccatcgagaa gaccatcagc    1080
aaggccaagg gccagccccg ggagcctcag gtgtacaccc tgccccccag ccgcgacgag    1140
ctgaccaaga accaggtgag cctgacctgc ctggtgaagg gcttctaccc ctccgacatc    1200
gccgtggagt gggagagcaa cggccagcct gagaacaact acaagaccac ccctcccgtg    1260
ctggacagcg acggcagctt cttcctgtac agcaagctga ccgtggacaa gtcccggtgg    1320
cagcagggca acgtgttcag ctgcagcgtg atgcacgagg ccctgcacaa ccactacacc    1380
cagaagagcc tgagcctgag ccccggatag taa                                 1413
```

<210> SEQ ID NO 7
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly

-continued

```
                20                  25                  30
Gly Gly Leu Val Gln Pro Gly Gly Ser Leu Arg Leu Ser Cys Ala Val
                35                  40                  45

Ser Gly Ile Asp Phe Ser Arg Tyr Trp Met Ser Trp Val Arg Gln Ala
        50                  55                  60

Pro Gly Lys Gly Leu Glu Trp Val Gly Glu Ile Thr Pro Asp Ser Asn
 65                  70                  75                  80

Thr Ile Asn Tyr Val Pro Ser Val Lys Gly Arg Phe Thr Ile Ser Arg
                    85                  90                  95

Asp Asn Ala Lys Asn Ser Leu Tyr Leu Gln Met Asn Ser Leu Arg Ala
                100                 105                 110

Glu Asp Thr Ala Val Tyr Tyr Cys Ala Ser Tyr Tyr Glu Gly Phe Ala
                115                 120                 125

Tyr Trp Gly Gln Gly Thr Leu Val Thr Val Ser Ala Ser Thr Lys
            130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
                195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Thr Cys Val Val Val Asp
                275                 280                 285

Val Ser His Glu Asp Pro Glu Val Lys Phe Asn Trp Tyr Val Asp Gly
            290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445
```

Ser Val Met His Glu Ala Leu His Asn His Tyr Thr Gln Lys Ser Leu
        450                 455                 460

Ser Leu Ser Pro Gly
465

<210> SEQ ID NO 8
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atggacccca agggcagcct gagctggaga atcctgctgt tcctgagcct ggccttcgag    60
ctgagctacg gcgaagtgca gctggtggaa tctggcggcg gactggtgca gcctggcgga   120
tctctgagac tgtcctgcgc cgtgtccggc atcgacttct cccggtactg gatgtcctgg   180
gtgcgacagg ctcctggcaa gggcctggaa tgggtgggag agatcacccc cgactccaac   240
accatcaact acgtgccctc cgtgaagggc cggttcacca tctccagaga caacgccaag   300
aactccctgt acctgcagat gaacagcctg cgggccgagg ataccgccgt gtactactgc   360
gcctcctact acgagggctt cgcctattgg ggccagggca ccctcgtgac cgtgtcctct   420
gctagcacca agggccccag cgtgttccct ctggccccca gcagcaagag caccagcggc   480
ggaaccgccg ccctgggctg cctggtgaag gactacttcc ccgagcccgt gaccgtgtcc   540
tggaacagcg gcgctctgac cagcggagtg cacaccttcc ctgccgtgct gcagagcagc   600
ggcctgtact ccctgagcag cgtggtgacc gtgcccagca gcagcctggg cacccagacc   660
tacatctgca acgtgaacca caagccctcc aacaccaagg tggacaagaa ggtggagcct   720
aagagctgcg acaagaccca cacctgccct cctgccccg cccccgagct gctgggcgga   780
cccagcgtgt tcctgttccc tcccaagccc aaggacaccc tgatgatcag ccgcacccc   840 gaggtgacct gcgtggtggt ggacgtgagc cacgaggacc ccgaggtgaa gttcaactgg   900
tacgtggacg gcgtggaggt gcacaacgcc aagaccaagc ccgggagga gcagtacaac   960 tccacctacc gcgtggtgag cgtgctgacc gtgctgcacc aggactggct gaacggcaag  1020
gagtacaagt gcaaggtgag caacaaggcc ctgcccgctc ccatcgagaa gaccatcagc  1080
aaggccaagg ccagccccg ggagcctcag gtgtacaccc tgcccccag ccgcgacgag  1140 ctgaccaaga accaggtgag cctgacctgc ctggtgaagg gcttctaccc ctccgacatc  1200
gccgtggagt gggagagcaa cggccagcct gagaacaact acaagaccac ccctcccgtg  1260
ctggacagcg acggcagctt cttcctgtac agcaagctga ccgtggacaa gtcccggtgg  1320
cagcagggca acgtgttcag ctgcagcgtg atgcacgagg ccctgcacaa ccactacacc  1380
cagaagagcc tgagcctgag ccccggatag taa                               1413

<210> SEQ ID NO 9
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Met Asp Pro Lys Gly Ser Leu Ser Trp Arg Ile Leu Leu Phe Leu Ser
1               5                   10                  15

```
Leu Ala Phe Glu Leu Ser Tyr Gly Glu Val Lys Leu Val Glu Ser Gly
            20                  25                  30

Gly Gly Leu Val Gln Pro Gly Gly Ser Leu Arg Leu Ser Cys Ala Val
            35                  40                  45

Ser Gly Ile Asp Phe Ser Arg Tyr Trp Met Ser Trp Val Arg Gln Ala
 50                  55                  60

Pro Gly Lys Gly Leu Glu Trp Val Gly Glu Ile Thr Pro Asp Ser Asn
 65                  70                  75                  80

Thr Ile Asn Tyr Val Pro Ser Val Lys Gly Arg Phe Thr Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Phe Cys Ala Ser Tyr Tyr Glu Gly Phe Ala
            115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
            165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
            210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
            245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
            275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
            325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
            370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
            405                 410                 415

Thr Pro Pro Val Leu Asp Ser Asp Gly Ser Phe Phe Leu Tyr Ser Lys
            420                 425                 430
```

Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly
465

<210> SEQ ID NO 10
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10

| | | | | | |
|---|---|---|---|---|---|
| atggacccca | agggcagcct | gagctggaga | atcctgctgt | tcctgagcct | ggccttcgag | 60 |
| ctgagctacg | cgaagtgaa | gctggtggaa | tctggcggcg | gactggtgca | gcctggcgga | 120 |
| tctctgagac | tgtcctgcgc | cgtgtccggc | atcgacttct | cccggtactg | gatgtcctgg | 180 |
| gtgcgacagg | ctcctggcaa | gggcctggaa | tgggtgggag | agatcacccc | cgactccaac | 240 |
| accatcaact | acgtgccctc | cgtgaagggc | cggttcacca | tctccagaga | caacgccaag | 300 |
| aactccctgt | acctgcagat | gaacagcctg | cgggccgagg | ataccgccgt | gtacttctgc | 360 |
| gcctcctact | acgagggctt | cgcctattgg | ggccagggca | ccctcgtgac | cgtgtcctct | 420 |
| gctagcacca | agggcccag | cgtgttccct | ctggccccca | gcagcaagag | caccagcggc | 480 |
| ggaaccgccg | ccctgggctg | cctggtgaag | gactacttcc | ccgagcccgt | gaccgtgtcc | 540 |
| tggaacagcg | gcgctctgac | cagcggagtg | cacaccttcc | ctgccgtgct | gcagagcagc | 600 |
| ggcctgtact | ccctgagcag | cgtggtgacc | gtgcccagca | gcagcctggg | cacccagacc | 660 |
| tacatctgca | acgtgaacca | caagccctcc | aacaccaagg | tggacaagaa | ggtggagcct | 720 |
| aagagctgcg | acaagaccca | cacctgccct | ccctgccccg | cccccgagct | gctgggcgga | 780 |
| cccagcgtgt | tcctgttccc | tcccaagccc | aaggacaccc | tgatgatcag | ccgcaccccc | 840 |
| gaggtgacct | gcgtggtggt | ggacgtgagc | cacgaggacc | ccgaggtgaa | gttcaactgg | 900 |
| tacgtggacg | gcgtggaggt | gcacaacgcc | aagaccaagc | ctcgggagga | gcagtacaac | 960 |
| tccacctacc | gcgtggtgag | cgtgctgacc | gtgctgcacc | aggactggct | gaacggcaag | 1020 |
| gagtacaagt | gcaaggtgag | caacaaggcc | ctgcccgctc | ccatcgagaa | gaccatcagc | 1080 |
| aaggccaagg | gccagccccg | ggagcctcag | gtgtacaccc | tgccccccag | ccgcgacgag | 1140 |
| ctgaccaaga | accaggtgag | cctgacctgc | ctggtgaagg | gcttctaccc | ctccgacatc | 1200 |
| gccgtggagt | gggagagcaa | cggccagcct | gagaacaact | acaagaccac | ccctcccgtg | 1260 |
| ctggacagcg | acggcagctt | cttcctgtac | agcaagctga | ccgtggacaa | gtcccggtgg | 1320 |
| cagcagggca | acgtgttcag | ctgcagcgtg | atgcacgagg | ccctgcacaa | ccactacacc | 1380 |
| cagaagagcc | tgagcctgag | ccccggatag | taa | | | 1413 |

<210> SEQ ID NO 11
<211> LENGTH: 469
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

```
Met Asp Pro Lys Gly Ser Leu Ser Trp Arg Ile Leu Leu Phe Leu Ser
1               5                   10                  15
Leu Ala Phe Glu Leu Ser Tyr Gly Glu Val Gln Leu Val Glu Ser Gly
            20                  25                  30
Gly Gly Leu Val Gln Pro Gly Gly Phe Leu Arg Leu Ser Cys Val Val
        35                  40                  45
Ser Gly Ile Asp Phe Ser Arg Tyr Trp Met Ser Trp Val Arg Gln Ala
50                  55                  60
Pro Gly Lys Gly Leu Glu Trp Val Gly Glu Ile Thr Pro Asp Ser Asn
65                  70                  75                  80
Thr Ile Asn Tyr Val Pro Ser Val Lys Gly Asn Phe Gly Ile Ser Arg
                85                  90                  95
Asp Asn Ala Lys Asn Ser Leu Phe Leu Gln Met Asn Ser Leu Arg Ala
            100                 105                 110
Glu Asp Thr Ala Val Tyr Phe Cys Ala Ser Tyr Tyr Glu Gly Phe Ala
        115                 120                 125
Tyr Trp Gly Gln Gly Thr Leu Val Thr Val Ser Ala Ser Thr Lys
    130                 135                 140
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
210                 215                 220
Val Asn His Lys Pro Ser Asn Thr Lys Val Asp Lys Lys Val Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Lys Pro Lys Asp
            260                 265                 270
Thr Leu Met Ile Ser Arg Thr Pro Glu Val Thr Cys Val Val Val Asp
        275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
```

Leu Thr Val Asp Lys Ser Arg Trp Gln Gln Gly Asn Val Phe Ser Cys
        420             425                 430
Ser Val Met His Glu Ala Leu His Asn His Tyr Thr Gln Lys Ser Leu
435                 440                 445

Ser Leu Ser Pro Gly
465

<210> SEQ ID NO 12
<211> LENGTH: 1413
<212> TYPE: DNA
<213> ORGANISM: Artificial Sequence
<220> FEATURE:
<223> OTHER INFORMATION: Description of Artificial Sequence: Synthetic
    polynucleotide

<400> SEQUENCE: 12

```
atggacccca agggcagcct gagctggaga atcctgctgt tcctgagcct ggccttcgag      60
ctgagctacg gcgaagtgca gctggtgaaa tctggcggcg gactggtgca gcctggcggc     120
tttctgagac tgtcctgcgt ggtgtccggc atcgacttct cccggtactg gatgtcctgg     180
gtgcgacagg ctcctggcaa gggcctggaa tgggtgggag agatcacccc cgactccaac     240
accatcaact acgtgccctc cgtgaagggc aacttcggca tctccagaga caacgccaag     300
aactccctgt tcctgcagat gaacagcctg cgggccgagg ataccgccgt gtacttctgc     360
gcctcctact acgagggctt cgcctattgg ggccagggca ccctcgtgac cgtgtcctct     420
gctagcacca agggccccag cgtgttccct ctggccccca gcagcaagag caccagcggc     480
ggaaccgccg ccctgggctg cctggtgaag gactacttcc ccgagcccgt gaccgtgtcc     540
tggaacagcg gcgctctgac cagcggagtg cacaccttcc ctgccgtgct gcagagcagc     600
ggcctgtact ccctgagcag cgtggtgacc gtgcccagca gcagcctggg cacccagacc     660
tacatctgca acgtgaacca caagccctcc aacaccaagg tggacaagaa ggtgagcct      720
aagagctgcg acaagaccca cacctgccct cctgccccg cccccgagct gctgggcgga     780
cccagcgtgt tcctgttccc tcccaagccc aaggacaccc tgatgatcag ccgcaccccc     840
gaggtgacct gcgtggtggt ggacgtgagc cacgaggacc ccgaggtgaa gttcaactgg     900
tacgtggacg gcgtggaggt gcacaacgcc aagaccaagc tcgggagga gcagtacaac     960
tccacctacc gcgtggtgag cgtgctgacc gtgctgcacc aggactggct gaacggcaag    1020
gagtacaagt gcaaggtgag caacaaggcc ctgcccgctc ccatcgagaa gaccatcagc    1080
aaggccaagg gccagccccg ggagcctcag gtgtacaccc tgcccccag ccgcgacgag    1140
ctgaccaaga accaggtgag cctgacctgc ctggtgaagg gcttctaccc ctccgacatc    1200
gccgtggagt gggagagcaa cggccagcct gagaacaact acaagaccac ccctcccgtg    1260
ctggacagcg acggcagctt cttcctgtac agcaagctga ccgtggacaa gtcccggtgg    1320
cagcagggca acgtgttcag ctgcagcgtg atgcacgagg ccctgcacaa ccactacacc    1380
cagaagagcc tgagcctgag ccccggatag taa                                 1413
```

<210> SEQ ID NO 13
<211> LENGTH: 469
<212> TYPE: PRT
<213> ORGANISM: Artificial Sequence
<220> FEATURE:
<223> OTHER INFORMATION: Description of Artificial Sequence: Synthetic
    polypeptide

```
<400> SEQUENCE: 13

Met Asp Pro Lys Gly Ser Leu Ser Trp Arg Ile Leu Leu Phe Leu Ser
1               5                   10                  15

Leu Ala Phe Glu Leu Ser Tyr Gly Glu Val Gln Leu Val Glu Ser Gly
            20                  25                  30

Gly Gly Leu Val Gln Pro Gly Gly Ser Leu Arg Leu Ser Cys Val Val
        35                  40                  45

Ser Gly Ile Asp Phe Ser Arg Tyr Trp Met Ser Trp Val Arg Gln Ala
50                  55                  60

Pro Gly Lys Gly Leu Glu Trp Val Gly Glu Ile Thr Pro Asp Ser Asn
65                  70                  75                  80

Thr Ile Asn Tyr Val Pro Ser Val Lys Gly Arg Phe Gly Ile Ser Arg
                85                  90                  95

Asp Asn Ala Lys Asn Ser Leu Tyr Leu Gln Met Asn Ser Leu Arg Ala
            100                 105                 110

Glu Asp Thr Ala Val Tyr Phe Cys Ala Ser Tyr Tyr Glu Gly Phe Ala
        115                 120                 125

Tyr Trp Gly Gln Gly Thr Leu Val Thr Val Ser Ser Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Val Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415
```

Thr Pro Pro Val Leu Asp Ser Asp Gly Ser Phe Phe Leu Tyr Ser Lys
             420                 425                 430

Leu Thr Val Asp Lys Ser Arg Trp Gln Gln Gly Asn Val Phe Ser Cys
         435                 440                 445

Ser Val Met His Glu Ala Leu His Asn His Tyr Thr Gln Lys Ser Leu
    450                 455                 460

Ser Leu Ser Pro Gly
465

<210> SEQ ID NO 14
<211> LENGTH: 1413
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 14

```
atggacccca agggcagcct gagctggaga atcctgctgt cctgagcct ggccttcgag      60 ctgagctacg gcgaagtgca gctggtggaa tctggcggcg gactggtgca gcctggcgga    120
tctctgagac tgtcctgcgt ggtgtccggc atcgacttct cccggtactg gatgtcctgg    180
gtgcgacagg ctcctggcaa gggcctggaa tgggtgggag agatcacccc cgactccaac    240
accatcaact acgtgccctc cgtgaagggc cggttcggca tctccagaga caacgccaag    300
aactccctgt acctgcagat gaacagcctg cgggccgagg ataccgccgt gtacttctgc    360
gcctcctact acgagggctt cgcctattgg ggccagggca cctcgtgac cgtgtcctct    420 gctagcacca agggcccag cgtgttccct ctggcccca gcagcaagag caccagcggc    480
ggaaccgccg ccctgggctg cctggtgaag gactacttcc ccgagcccgt gaccgtgtcc    540
tggaacagcg gcgctctgac cagcggagtg cacaccttcc ctgccgtgct gcagagcagc    600
ggcctgtact ccctgagcag cgtggtgacc gtgcccagca gcagcctggg cacccagacc    660
tacatctgca acgtgaacca caagccctcc aacaccaagg tggacaagaa ggtggagcct    720
aagagctgcg acaagaccca cacctgccct cctgccccg cccccgagct gctgggcgga    780
cccagcgtgt tcctgttccc tcccaagccc aaggacaccc tgatgatcag ccgcacccc    840 gaggtgacct gcgtggtggt ggacgtgagc cacgaggacc ccgaggtgaa gttcaactgg    900
tacgtggacg gcgtggaggt gcacaacgcc aagaccaagc ctcgggagga gcagtacaac    960
tccacctacc gcgtggtgag cgtgctgacc gtgctgcacc aggactggct gaacggcaag   1020
gagtacaagt gcaaggtgag caacaaggcc ctgcccgctc ccatcgagaa gaccatcagc   1080
aaggccaagg gccagccccg ggagcctcag gtgtacaccc tgcccccag ccgcgacgag   1140 ctgaccaaga accaggtgag cctgacctgc ctggtgaagg gcttctaccc ctccgacatc   1200
gccgtggagt gggagagcaa cggccagcct gagaacaact acaagaccac ccctcccgtg   1260
ctggacagcg acggcagctt cttcctgtac agcaagctga ccgtggacaa gtcccggtgg   1320
cagcagggca acgtgttcag ctgcagcgtg atgcacgagg ccctgcacaa ccactacacc   1380
cagaagagcc tgagcctgag ccccggatag taa                                1413
```

<210> SEQ ID NO 15
<211> LENGTH: 235
<212> TYPE: PRT
<213> ORGANISM: Artificial Sequence
<220> FEATURE:
<223> OTHER INFORMATION: Description of Artificial Sequence: Synthetic -continued polypeptide

<400> SEQUENCE: 15

Met Ser Val Pro Thr Gln Val Leu Gly Leu Leu Leu Trp Leu Thr
1               5                   10                  15

Asp Ala Arg Cys Gln Ala Val Val Thr Gln Glu Pro Ser Leu Thr Val
            20                  25                  30

Ser Pro Gly Gly Thr Val Thr Leu Thr Cys Gly Ser Ser Thr Gly Ala
        35                  40                  45

Val Ile Thr Ser Asn Tyr Ala Asn Trp Phe Gln Gln Lys Pro Gly Gln
    50                  55                  60

Ala Pro Arg Thr Leu Ile Gly Arg Thr Tyr Asn Lys Val Pro Trp Thr
65                  70                  75                  80

Pro Ala Arg Phe Ser Gly Ser Leu Leu Gly Gly Lys Ala Ala Leu Thr
                85                  90                  95

Leu Ser Gly Ala Gln Pro Glu Asp Glu Ala Glu Tyr Tyr Cys Ala Leu
            100                 105                 110

Trp Tyr Ser Asn His Phe Val Phe Gly Gly Gly Thr Lys Leu Thr Val
        115                 120                 125

Leu Gly Gln Pro Lys Ala Ala Pro Ser Val Thr Leu Phe Pro Pro Ser
    130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235

<210> SEQ ID NO 16
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 16
atgtccgtgc ctacccaggt gctgggactg ctgctgctgt ggctgaccga cgccagatgt      60
caggctgtcg tgacccagga accttccctg accgtgtctc ctggcggcac cgtgaccctg     120
acctgtggat cttctaccgg cgctgtgatc acctccaact acgccaactg gttccagcag     180
aagccaggcc aggctcctag aaccctgatc ggcagaacct acaacaaggt gccatggacc     240
cctgcccggt tctccggatc tctgctggga ggaaaggccg ctctgaccct gtctggtgcc     300
cagcctgagg atgaggccga gtactactgc gccctgtggt actccaacca cttcgtgttc     360
ggcggaggca ccaagctgac cgtgctggga cagcctaagg ccgctccttc cgtgaccctg     420
ttccctccat cctccgagga actgcaggcc aacaaggcca ccctcgtgtg cctgatctcc     480
gacttctacc ctggcgccgt gaccgtggcc tggaaggcta tagctctcc tgtgaaggcc     540
ggcgtggaaa ccaccacccc ttccaagcag tccaacaaca atacgccgc ctcctcctac     600

```
ctgtccctga ccoctgagca gtggaagtcc caccggtcct acagctgcca agtgacccac      660
gagggctcca ccgtggaaaa gaccgtggct cctaccgagt gctcctgata a              711
```

<210> SEQ ID NO 17
<211> LENGTH: 235
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

```
Met Ser Val Pro Thr Gln Val Leu Gly Leu Leu Leu Leu Trp Leu Thr
1               5                   10                  15

Asp Ala Arg Cys Gln Ala Val Val Thr Gln Glu Pro Ser Leu Thr Val
                20                  25                  30

Ser Pro Gly Gly Thr Val Thr Leu Thr Cys Gly Ser Ser Thr Gly Ala
            35                  40                  45

Val Ile Thr Ser Asn Tyr Ala Asn Trp Val Gln Gln Lys Pro Gly Gln
        50                  55                  60

Ala Pro Thr Gly Leu Ile Gly Arg Thr Tyr Asn Lys Val Pro Trp Thr
65                  70                  75                  80

Pro Ala Arg Phe Ser Gly Ser Leu Leu Gly Asp Lys Ala Ala Leu Thr
                85                  90                  95

Leu Ser Gly Ala Gln Pro Glu Asp Glu Ala Glu Tyr Phe Cys Ala Leu
            100                 105                 110

Trp Tyr Ser Asn His Phe Val Phe Gly Gly Gly Thr Lys Leu Thr Val
        115                 120                 125

Leu Gly Gln Pro Lys Ala Ala Pro Ser Val Thr Leu Phe Pro Pro Ser
130                 135                 140

Ser Glu Glu Leu Gln Ala Asn Lys Ala Thr Leu Val Cys Leu Ile Ser
145                 150                 155                 160

Asp Phe Tyr Pro Gly Ala Val Thr Val Ala Trp Lys Ala Asp Ser Ser
                165                 170                 175

Pro Val Lys Ala Gly Val Glu Thr Thr Thr Pro Ser Lys Gln Ser Asn
            180                 185                 190

Asn Lys Tyr Ala Ala Ser Ser Tyr Leu Ser Leu Thr Pro Glu Gln Trp
        195                 200                 205

Lys Ser His Arg Ser Tyr Ser Cys Gln Val Thr His Glu Gly Ser Thr
    210                 215                 220

Val Glu Lys Thr Val Ala Pro Thr Glu Cys Ser
225                 230                 235
```

<210> SEQ ID NO 18
<211> LENGTH: 711
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 18

```
atgtccgtgc ctacccaggt gctgggactg ctgctgctgt ggctgaccga cgccagatgt      60
caggctgtcg tgacccagga accttccctg accgtgtctc ctggcggcac cgtgaccctg      120
acctgtggat cttctaccgg cgctgtgatc acctccaact acgccaactg ggtgcagcag      180
aagccaggcc aggctcctac cggcctgatc ggcagaacct acaacaaggt gccatggacc      240
```

```
cctgcccggt tctccggatc tctgctgggc gataaggccg ctctgaccct gtctggtgcc       300
cagcctgagg atgaggccga gtacttctgc gccctgtggt actccaacca cttcgtgttc       360
ggcggaggca ccaagctgac cgtgctggga cagcctaagg ccgctccttc cgtgaccctg       420
ttccctccat cctccgagga actgcaggcc aacaaggcca ccctcgtgtg cctgatctcc       480
gacttctacc ctggcgccgt gaccgtggcc tggaaggctg atagctctcc tgtgaaggcc       540
ggcgtggaaa ccaccacccc ttccaagcag tccaacaaca aatacgccgc ctcctcctac       600
ctgtccctga cccctgagca gtggaagtcc accggtcct acagctgcca agtgacccac       660
gagggctcca ccgtggaaaa gaccgtggct cctaccgagt gctcctgata a               711
```

<210> SEQ ID NO 19
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

Glu Val Lys Leu His Gln Ser Gly Gly Gly Leu Val Gln Pro Gly Gly
1               5                   10                  15

Phe Leu Lys Ile Ser Cys Val Val Ser Gly Ile Asp Phe Ser Arg Tyr
            20                  25                  30

Trp Met Ser Trp Val Arg Arg Ala Pro Gly Lys Gly Leu Glu Trp Ile
        35                  40                  45

Gly Glu Ile Thr Pro Asp Ser Asn Thr Ile Asn Tyr Val Pro Ser Leu
    50                  55                  60

Lys Asp Asn Phe Gly Ile Ser Arg Asp Asn Ala Lys Asn Thr Leu Phe
65                  70                  75                  80

Leu Gln Met Thr Lys Val Arg Ser Glu Asp Thr Ala Leu Tyr Phe Cys
                85                  90                  95

Ala Ser Tyr Tyr Glu Gly Phe Ala Tyr Trp Gly Gln Gly Thr Leu Val
            100                 105                 110

Thr Val Ser Ala
        115

<210> SEQ ID NO 20
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Ile Thr Ser
            20                  25                  30

Asn Tyr Ala Asn Trp Val Gln Glu Lys Pro Asp His Leu Phe Thr Gly
        35                  40                  45

Leu Ile Gly Arg Thr Tyr Asn Arg Val Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn

His Phe Val Phe Gly Gly Gly Thr Lys Leu Thr Val Leu
            100                 105

<210> SEQ ID NO 21
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Ala Glu Ile Thr Pro Asp Ser Asn Thr Ile Asn Tyr Val Pro Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Tyr Tyr Glu Gly Phe Ala Tyr Trp Gly Gln Gly Thr Leu Val
            100                 105                 110

Thr Val Ser Ser
        115

<210> SEQ ID NO 22
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Val Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Gly Glu Ile Thr Pro Asp Ser Asn Thr Ile Asn Tyr Val Pro Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Ser Tyr Tyr Glu Gly Phe Ala Tyr Trp Gly Gln Gly Thr Leu Val
            100                 105                 110

Thr Val Ser Ser
        115

<210> SEQ ID NO 23
<211> LENGTH: 116
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 23

Glu Val Lys Leu Val Glu Ser Gly Gly Gly Leu Val Gln Pro Gly Gly
1               5                   10                  15

Ser Leu Arg Leu Ser Cys Ala Val Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Gly Glu Ile Thr Pro Asp Ser Asn Thr Ile Asn Tyr Val Pro Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Phe Cys
                85                  90                  95

Ala Ser Tyr Tyr Glu Gly Phe Ala Tyr Trp Gly Gln Gly Thr Leu Val
            100                 105                 110

Thr Val Ser Ser
        115

<210> SEQ ID NO 24
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Val Gln Leu Val Glu Ser Gly Gly Gly Leu Val Gln Pro Gly Gly
1               5                   10                  15

Phe Leu Arg Leu Ser Cys Val Val Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Gly Glu Ile Thr Pro Asp Ser Asn Thr Ile Asn Tyr Val Pro Ser Val
    50                  55                  60

Lys Gly Asn Phe Gly Ile Ser Arg Asp Asn Ala Lys Asn Ser Leu Phe
65                  70                  75                  80

Leu Gln Met Asn Ser Leu Arg Ala Glu Asp Thr Ala Val Tyr Phe Cys
                85                  90                  95

Ala Ser Tyr Tyr Glu Gly Phe Ala Tyr Trp Gly Gln Gly Thr Leu Val
            100                 105                 110

Thr Val Ser Ser
        115

<210> SEQ ID NO 25
<211> LENGTH: 116
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Glu Val Gln Leu Val Glu Ser Gly Gly Gly Leu Val Gln Pro Gly Gly
1               5                   10                  15
```

```
Ser Leu Arg Leu Ser Cys Val Val Ser Gly Ile Asp Phe Ser Arg Tyr
            20                  25                  30

Trp Met Ser Trp Val Arg Gln Ala Pro Gly Lys Gly Leu Glu Trp Val
        35                  40                  45

Gly Glu Ile Thr Pro Asp Ser Asn Thr Ile Asn Tyr Val Pro Ser Val
 50                  55                  60

Lys Gly Arg Phe Gly Ile Ser Arg Asp Asn Ala Lys Asn Ser Leu Tyr
 65                  70                  75                  80

Leu Gln Met Asn Ser Leu Arg Ala Glu Asp Thr Ala Val Tyr Phe Cys
                85                  90                  95

Ala Ser Tyr Tyr Glu Gly Phe Ala Tyr Trp Gly Gln Gly Thr Leu Val
               100                 105                 110

Thr Val Ser Ser
       115

<210> SEQ ID NO 26
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Ile Thr Ser
            20                  25                  30

Asn Tyr Ala Asn Trp Phe Gln Gln Lys Pro Gly Gln Ala Pro Arg Thr
        35                  40                  45

Leu Ile Gly Arg Thr Tyr Asn Lys Val Pro Trp Thr Pro Ala Arg Phe
 50                  55                  60

Ser Gly Ser Leu Leu Gly Gly Lys Ala Ala Leu Thr Leu Ser Gly Ala
 65                  70                  75                  80

Gln Pro Glu Asp Glu Ala Glu Tyr Tyr Cys Ala Leu Trp Tyr Ser Asn
                85                  90                  95

His Phe Val Phe Gly Gly Gly Thr Lys Leu Thr Val Leu
               100                 105

<210> SEQ ID NO 27
<211> LENGTH: 109
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Gln Ala Val Val Thr Gln Glu Pro Ser Leu Thr Val Ser Pro Gly Gly
 1               5                  10                  15

Thr Val Thr Leu Thr Cys Gly Ser Ser Thr Gly Ala Val Ile Thr Ser
            20                  25                  30

Asn Tyr Ala Asn Trp Val Gln Gln Lys Pro Gly Gln Ala Pro Thr Gly
        35                  40                  45

Leu Ile Gly Arg Thr Tyr Asn Lys Val Pro Trp Thr Pro Ala Arg Phe
 50                  55                  60

Ser Gly Ser Leu Leu Gly Asp Lys Ala Ala Leu Thr Leu Ser Gly Ala
 65                  70                  75                  80
```

```
Gln Pro Glu Asp Glu Ala Glu Tyr Phe Cys Ala Leu Trp Tyr Ser Asn
                85                  90                  95

His Phe Val Phe Gly Gly Gly Thr Lys Leu Thr Val Leu
            100                 105

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Gly Ile Asp Phe Ser Arg Tyr Trp
1               5

<210> SEQ ID NO 29
<211> LENGTH: 8
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 29

Ile Thr Pro Asp Ser Asn Thr Ile
1               5

<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Ala Ser Tyr Tyr Glu Gly Phe Ala Tyr
1               5

<210> SEQ ID NO 31
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

Thr Gly Ala Val Ile Thr Ser Asn Tyr
1               5

<210> SEQ ID NO 32
<211> LENGTH: 3
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 32

Arg Thr Tyr
1

<210> SEQ ID NO 33
```

```
<211> LENGTH: 9
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

Ala Leu Trp Tyr Ser Asn His Phe Val
1               5

<210> SEQ ID NO 34
<211> LENGTH: 13
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (6)..(6)
<223> OTHER INFORMATION: GalNAc modified

<400> SEQUENCE: 34

Arg Pro Ala Pro Gly Ser Thr Ala Pro Pro Ala His Gly
1               5                  10

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
gggrccarkg gatagachga tgg                                              23

<210> SEQ ID NO 36
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cttcagagga agggtggaaa cagg                                             24
```